(12) United States Patent  
Kim et al.

(10) Patent No.: US 11,769,594 B2  
(45) Date of Patent: Sep. 26, 2023

(54) DEEP LEARNING MODEL LEARNING DEVICE AND METHOD FOR CANCER REGION

(71) Applicant: JLK INC., Cheongju-si (KR)

(72) Inventors: Won Tae Kim, Suwon-si (KR); Shin Uk Kang, Seoul (KR); Myung Jae Lee, Seoul (KR); Dong Min Kim, Seoul (KR); Jin Seong Jang, Seoul (KR)

(73) Assignee: JLK INC., Cheongju-si (KR)

( * ) Notice: Subject to any disclaimer, the term of this patent is extended or adjusted under 35 U.S.C. 154(b) by 305 days.

(21) Appl. No.: 17/284,778

(22) PCT Filed: Oct. 11, 2019

(86) PCT No.: PCT/KR2019/013398  
§ 371 (c)(1),  
(2) Date: Apr. 12, 2021

(87) PCT Pub. No.: WO2020/076135  
PCT Pub. Date: Apr. 16, 2020

(65) Prior Publication Data  
US 2021/0391078 A1   Dec. 16, 2021

(30) Foreign Application Priority Data

Oct. 11, 2018 (KR) .................. 10-2018-0121393  
Oct. 12, 2018 (KR) .................. 10-2018-0121513

(51) Int. Cl.  
*G06K 9/00* (2022.01)  
*G16H 50/20* (2018.01)  
(Continued)

(52) U.S. Cl.  
CPC ............. *G16H 50/20* (2018.01); *A61B 5/055* (2013.01); *A61B 5/7267* (2013.01); *G06N 3/08* (2013.01);  
(Continued)

(58) Field of Classification Search  
CPC ........ G16H 50/20; G16H 30/20; G16H 50/70; G16H 30/40; A61B 5/055; A61B 5/7267;  
(Continued)

(56) References Cited

U.S. PATENT DOCUMENTS

2019/0102516 A1* 4/2019 Schieke ................. G16H 50/70

FOREIGN PATENT DOCUMENTS

EP          3367331 A1     8/2018  
KR   1020090111160 A    10/2009  
(Continued)

OTHER PUBLICATIONS

R. Trigui et al. "Automatic classification and localization of prostate cancer using multi-parametric MRI/MRS." Article. Aug. 17, 2016. Elsevier Ltd.  
(Continued)

*Primary Examiner* — Xin Jia  
(74) *Attorney, Agent, or Firm* — BROADVIEW IP LAW, PC

(57) ABSTRACT

A deep learning model learning device is proposed, including: a parametric MRI image input part inputting an image corresponding to a diagnosis region, inputting at least one parametric MRI image constructed on the basis of parameters different from each other, and constructing and providing an MRI moving image by using the at least one parametric MRI image; a cancer detection model learning part receiving an input of the at least one parametric MRI image and the MRI moving image corresponding to the diagnosis region, and learning a deep learning model on the  
(Continued)

basis of information labeling the cancer region; a labeling reference information providing part providing at least one reference information contributing to the labeling of the cancer region; and a labeling processing part checking the cancer region input on the basis of the at least one reference information and processing the labeling of the checked cancer region.

6 Claims, 20 Drawing Sheets

(51) Int. Cl.
*G16H 30/20* (2018.01)
*A61B 5/055* (2006.01)
*A61B 5/00* (2006.01)
*G06N 3/08* (2023.01)
*G06T 7/00* (2017.01)

(52) U.S. Cl.
CPC .......... *G06T 7/0014* (2013.01); *G16H 30/20* (2018.01); *A61B 2576/00* (2013.01); *G06T 2207/10016* (2013.01); *G06T 2207/10088* (2013.01); *G06T 2207/20081* (2013.01); *G06T 2207/30081* (2013.01)

(58) Field of Classification Search
CPC .... A61B 2576/00; G06N 3/08; G06T 7/0014; G06T 2207/10016; G06T 2207/10088; G06T 2207/20081; G06T 2207/30081; G06T 2207/10056; G06T 2207/10092; G06T 2207/10096; G06T 7/0012; G06T 7/11; G06T 7/194; G06T 2207/20084; G06T 2207/30056
See application file for complete search history.

(56) References Cited

FOREIGN PATENT DOCUMENTS

| KR | 101864412 B1 | 6/2018 | | |
|---|---|---|---|---|
| KR | 1020180082817 A | 7/2018 | | |
| KR | 1020180110355 A | 10/2018 | | |
| WO | WO-2009058915 A1 * | 5/2009 | ........... | G06K 9/4619 |
| WO | WO-2019200745 A1 * | 10/2019 | ........... | G06N 3/0454 |

OTHER PUBLICATIONS

Automated Prostate Cancer Detection on Multi-parametric MR imaging via Texture Analysis.

* cited by examiner

DEEP LEARNING MODEL LEARNING DEVICE AND METHOD FOR CANCER REGION

TECHNICAL FIELD

The present disclosure relates to a deep learning model learning technology and, more specifically, to a device and method for learning a cancer region in a specific body region on the basis of image information analysis.

BACKGROUND ART

Deep learning is to learn a very large amount of data, so that when new data is input, the answer with the highest probability is chosen on the basis of the learning result. Such deep learning may be operated adaptively depending on images, and since deep learning automatically finds a characteristic factor in the process of learning a model on the basis of the data, attempts to utilize deep learning in the field of artificial intelligence are increasing in recent years.

Meanwhile, regarding image recognition, a conventional image analysis technology that utilizes deep learning extracts local features for each region of an image by using a convolutional neural network (CNN) technique and a max pooling technique and recognizes the image on the basis of the local features. However, these techniques have a problem in that an accurate recognition result is not provided for an image having contents different from an actual image but similar local information types.

DISCLOSURE

Technical Problem

Meanwhile, by applying various parameters to an MRI (magnetic resonance imaging) image of a user's or a patient's body, various images, that is, parametric MRI images, may be reconstructed. Such parametric MRI images may be used as an important factor indicating changes in the body or disease.

However, conditions of the user or patient for a specific disease may appear in various ways, and the disease may also exhibit various characteristics or types. Therefore, there is a problem in that it is difficult to formalize a correlation between information represented by the parametric MRI image and a change or disease in the body.

The technical problem of the present disclosure relates to a method and device for learning a relationship between various parametric MRI images and specific diseases on the basis of local characteristics and global context of the images.

Another technical problem of the present disclosure relates to the method and device for learning a region where cancer occurs on the basis of a parametric MRI image for a diagnosis region.

Yet another technical problem of the present disclosure relates to the method and device for learning the region where cancer occurs on the basis of the parametric MRI image and reference information for the diagnosis region.

The technical problems to be achieved in the present disclosure are not limited to the technical problems mentioned above, and other technical problems that are not mentioned will be clearly understood by those skilled in the art to which the present disclosure belongs from the following description.

Technical Solution

According to an aspect of the present disclosure, a deep learning model learning device for a cancer region may be provided. The deep learning model learning device may include: a parametric MRI image input part for inputting an image corresponding to a diagnosis region, inputting at least one parametric MRI image constructed on the basis of parameters different from each other, and constructing and providing an MRI moving image by using the at least one parametric MRI image; a cancer detection model learning part for receiving an input of the at least one parametric MRI image and the MRI moving image corresponding to the diagnosis region, and learning a deep learning model on the basis of information labeling the cancer region; a labeling reference information providing part for providing at least one reference information contributing to the labeling of the cancer region; and a labeling processing part for checking the cancer region input on the basis of the at least one reference information and processing the labeling of the checked cancer region.

Features briefly summarized above with respect to the present disclosure are only exemplary aspects of the detailed description of the present disclosure described below, and do not limit the scope of the present disclosure.

Advantageous Effects

According to the present disclosure, a method and device for learning a relationship between various parametric MRI images and specific diseases on the basis of local features and global context of the images may be provided.

In addition, according to the present disclosure, the method and device for learning a region where cancer occurs on the basis of the parametric MRI image for a diagnosis region may be provided.

In addition, according to the present disclosure, the method and device for learning the region where cancer occurs on the basis of the parametric MRI image and reference information for the diagnosis region may be provided.

The effects of the present disclosure are not limited to the above-mentioned effects, and other different effects that are not mentioned will be clearly understood by those skilled in the art from the following description.

MODE FOR INVENTION

Figure 1:
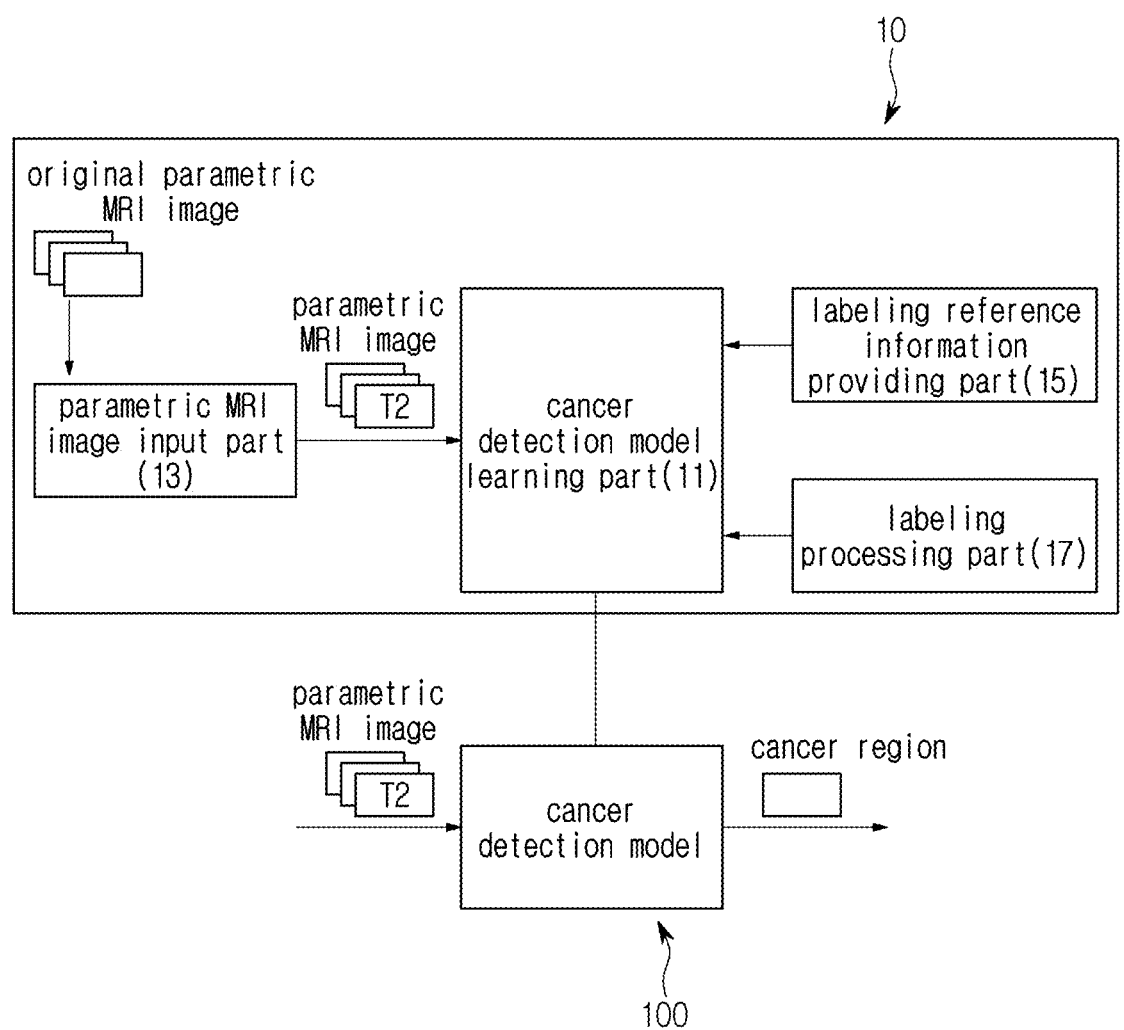
FIG. 1 is a block diagram showing a configuration of a deep learning model learning device according to an exemplary embodiment of the present disclosure.

Hereinafter, exemplary embodiments of the present disclosure will be described in detail with reference to the accompanying drawings so that those skilled in the art can easily implement the present disclosure. However, the present disclosure may be implemented in various different forms and is not limited to the exemplary embodiments described herein.

In describing the exemplary embodiment of the present disclosure, when it is determined that a detailed description of a known configuration or function may obscure the subject matter of the present disclosure, the detailed description thereof will be omitted. In addition, parts not related to the description of the present disclosure in the drawings are omitted, and similar reference numerals are used to similar parts.

In the present disclosure, when a component is said to be "connected", "coupled", or "linked" with another component, this may include not only a direct connection, but also an indirect connection in which another component exists in the middle therebetween. In addition, when a component "includes" or "has" other components, it means that other components may be further included rather than excluding other components unless the context clearly indicates otherwise.

In the present disclosure, terms such as first and second are used only for the purpose of distinguishing one component from other components, and do not limit the order, importance, or the like of components unless otherwise noted. Accordingly, within the scope of the present disclosure, a first component in one exemplary embodiment may be referred to as a second component in another exemplary embodiment, and similarly, a second component in one exemplary embodiment may also be referred to as a first component in another exemplary embodiment.

In the present disclosure, components that are distinguished from each other are intended to clearly describe each of their characteristics, and do not necessarily mean that the components are separated from each other. That is, a plurality of components may be integrated into one hardware or software unit, or one component may be distributed to be configured in a plurality of hardware or software units. Therefore, even when not stated otherwise, such integrated or distributed exemplary embodiments are also included in the scope of the present disclosure.

In the present disclosure, components described in various exemplary embodiments do not necessarily mean essential components, and some may be optional components. Accordingly, an exemplary embodiment consisting of a subset of components described in an exemplary embodiment is also included in the scope of the present disclosure. In addition, exemplary embodiments including other components in addition to the components described in the various exemplary embodiments are included in the scope of the present disclosure.

Hereinafter, exemplary embodiments of the present disclosure will be described with reference to the accompanying drawings.

FIG. 1 is a block diagram showing a configuration of a deep learning model learning device according to an exemplary embodiment of the present disclosure.

Referring to FIG. 1, the deep learning model learning device 10 may include: a cancer detection model learning part 11, a parametric MRI image input part 13, a labeling reference information providing part 15, and a labeling processing part 17.

First, the cancer detection model learning part 11 may perform learning of a cancer detection model on the basis of a convolutional neural network (CNN) technique or a pooling technique. In particular, the cancer detection model learning part 11 may receive an input of an analysis target image in order to perform the learning of the cancer detection model, and may perform a labeling operation, that is, an operation of receiving an input of a specific object or a specific region, included in the analysis target image, as a cancer region.

In addition, the cancer detection model learning part 11 may learn the cancer detection model by extracting features of the analysis target image and generating predetermined context information on the basis of the extracted features. In addition, the cancer detection model learning part 11 may construct a cancer detection model 100 by repeatedly performing the learning of the cancer detection model.

The cancer detection model learning part 11 may receive an input of an MRI image as an analysis target image, and such an input of the analysis target image may be processed by the parametric MRI image input part 13. The parametric MRI image input part 13 may provide an image of a user's body photographed by an MRI (magnetic resonance imaging) device, that is, the MRI image, to the cancer detection model learning part 11.

Furthermore, various images may be reconstructed by applying various parameters to an MRI image. In the exemplary embodiment of the present disclosure, an image reconstructed by applying a predetermined parameter to the MRI image is indicated as a parametric MRI image.

Based on this definition, the parametric MRI image input part 13 may provide at least one parametric MRI image constructed on the basis of parameters different from each other to the cancer detection model learning part 11. Here, the at least one parametric MRI image may include: a T1 (T1-weighted) image, a T2 (T2-weighted) image, a T2* (T2 star) image, an ADC (apparent diffusion coefficients) image, a FLAIR (fluid attenuated inversion recovery) image, a STIR (short TI inversion recovery) image, a PWI (perfusion weighted image), etc.

Furthermore, the cancer detection model learning part 11 may learn the cancer detection models for various body organs or diagnosis regions provided in the body of a user (or patient), and at least one parametric MRI image may be selectively used on the basis of the characteristics of each body organ or each diagnosis region, or the cancer region present in the body organ or the diagnosis region. To this end, the parametric MRI image input part 13 may selectively input at least one parametric MRI image corresponding to the body organ or diagnosis region to the cancer detection model learning part 11.

For example, in a case where a body organ or a diagnosis region is a prostate region, the parametric MRI image input part 13 may input a T2 (T2-weighted) image, an ADC (apparent diffusion coefficients) image, etc. As another example, in a case where a body organ or a diagnosis region is a liver region, the parametric MRI image input part 13 may input a STIR image, a T1 image, a T1 with agents image, a T2 image, etc. As yet another example, in a case where a body organ or a diagnosis region is a brain region, the parametric MRI image input part 13 may input a T1 image, a T2 image, a FLAIR image, etc.

In addition, the parametric MRI image input part 13 may display a parametric MRI image, providing an MRI image to the cancer detection model learning part 11, on a display and the like.

Additionally, the parametric MRI image input part 13 may receive an input of a parametric MRI image (hereinafter, referred to as "original parametric MRI image") based on the MRI image photographing the body where a user's diagnosis region is located, and may detect a parametric MRI image (hereinafter, referred to as "parametric MRI image of diagnosis region") extracting the diagnosis region from the original parametric MRI image. In addition, the parametric MRI image of the diagnosis region may be provided to the cancer detection model learning part 11 or may be displayed on a display and the like.

The operation of the parametric MRI image input part 13 to extract the parametric MRI image of the diagnosis region from the original parametric MRI image may be performed on the basis of the convolutional neural network (CNN) technique, the pooling technique, or the like. For example, the parametric MRI image input part 13 may construct a predetermined learning model through the learning in which the original parametric MRI image is input and the parametric MRI image of the diagnosis region is output. In addition, as the original parametric MRI image is input, the parametric MRI image input part 13 may detect and output the parametric MRI image of a diagnosis region.

Meanwhile, the labeling reference information providing part 15 may provide information contributing to a labeling process of the cancer region.

A diagnosis region of a user (or patient) may be excised through surgery, and a pathology image visualizing the region where cancer tissue is present may be constructed from the excised diagnosis region. In consideration of this way, the labeling reference information providing part 15 may provide an environment in which the pathology image may be input, and may display the received pathology image on a display and the like. For example, the pathology image may include the image in which a pathology map that maps a cancer-existing region of the extracted diagnosis region is constructed in an image format.

Furthermore, since the T2 image, the ADC image, or the like is composed of a two-dimensional image, it may be difficult to check cancer tissue present in a region not displayed on an image itself. In consideration of this fact, the labeling reference information providing part 15 checks a DWI (Diffusion-weighted imaging) image indicating information in which water molecules contained in the tissue are diffused in a specific direction, and may display the DWI image on a display and the like. Here, the DWI image may be provided from an MRI device, or may be obtained by processing the MRI image provided by the MRI device.

Likewise, since the T2 image or the ADC image is composed of the two-dimensional image, it may be difficult to check the tissue characteristics or the cancer tissue present in a region not displayed on an image itself. In consideration of this fact, the labeling reference information providing part 15 may check DCE (Dynamic Contrast Enhanced) signal information and establish an environment capable of providing the checked DCE signal information. For example, the labeling processing part 17 may provide an indicator for displaying a region designated by a user while displaying at least one parametric MRI image (e.g., T2 image), and the region selected by the user may be set as a cancer region. In consideration of the above description, the labeling reference information providing part 15 checks DCE signal information for the region indicated by the indicator generated and displayed by the labeling processing part 17, and may display the checked DCE signal information on a display and the like.

The labeling reference information providing part 15 may display at least one reference information (e.g., pathology image, DWI image, DCE signal information, etc.) on a display and the like.

As another example, the labeling reference information providing part 15 may sequentially select and display at least one reference information (e.g., pathology image, DWI image, DCE signal information, etc.). In particular, the labeling reference information providing part 15 may sequentially select and display the pathology image, DWI image, and DCE signal information in conjunction with the labeling processing part 17. For example, the labeling reference information providing part 15 may display a pathology image together with a T2 image and an ADC image. In addition, in a state in which the pathology image is displayed, as the information firstly labeling a cancer region is input by the labeling processing part 17, the labeling reference information providing unit 15 may display the DWI image together with the T2 image and the ADC image. In addition, in a state in which the DWI image is displayed, as the information secondly labeling the cancer region is input by the labeling processing part 17, the labeling reference information providing part 15 checks the region indicated by the indicator, and may check and display the DCE signal information corresponding to the relevant region.

In the exemplary embodiment of the present disclosure, as the labeling reference information providing part 15 is exemplified to sequentially provide at least one reference information, the at least one reference information is exemplified as the pathology image, DWI image, DCE signal information, etc. However, the present disclosure is not limited thereto, and various changes may be made thereto by those skilled in the art of the present disclosure. In addition, it is apparent that the order of the at least one reference information provided by the labeling reference information providing part 15 may also be variously changed.

Furthermore, according to the characteristics of each body organ or each diagnosis region, or a cancer region present in the body organ or diagnosis region, the information that may be used as reference information for labeling (i.e., reference information) may be variously changed. Accordingly, the labeling reference information providing part 15 may selectively provide the reference information that contributes to the labeling processing of the cancer region on the basis of the characteristics of each body organ or each diagnosis region, or the cancer region present in the body organ or diagnosis region.

For example, in the case where a body organ or a diagnosis region is a prostate region, the labeling reference information providing part 15 may provide a T1 contrast image, a T2 contrast image, a PET (positron emission tomography) image, a SPECT (single photon emission computed tomography) image, a DSA (digital subtraction angiography) image, and the like, as reference information. As another example, in the case where a body organ or a diagnosis region is a liver region, the labeling reference information providing part 15 may provide a T1 contrast image, a T2 contrast image, and the like, as reference information. As yet another example, in the case where a body organ or a diagnosis region is a brain region, the labeling reference information providing part 15 may provide FDG-PET image, SPECT image, and the like, as reference information.

Meanwhile, as described above, while providing at least one parametric MRI image (e.g., T2 image), the labeling processing part 17 may provide an environment in which an operation for designating an output value for learning a cancer detection model by the cancer detection model learning part 11, that is, the labeling, may be performed.

Specifically, the labeling processing part 17 outputs at least one parametric MRI image (e.g., T2 image) on a display, and may provide an interface capable of receiving a cancer region as an input, that is, a region where cancer is present in at least one parametric MRI image (e.g., T2 image) that is output. For example, the labeling processing part 17 may be connected to an external input device such as a mouse device, a digitizer device, a touch screen device, and the like, outputs a predetermined indicator to a region designated by the external input device, and sets the region, which is selected through the external input device, as a prostate cancer region.

Hereinafter, an operation of the above-described deep learning model learning device will be described with reference to FIGS. 1 and 2a to 2e.

In the description of the operation of the deep learning model learning device according to the exemplary embodiment of the present disclosure, the diagnosis region is exemplified as a prostate region, the cancer present in the diagnosis region is exemplified as prostate cancer, and the region where cancer is present is exemplified as a prostate cancer region.

FIGS. 2a to 2e are views showing information processed by an operation of the deep learning model learning device according to the exemplary embodiment of the present disclosure.

First, the parametric MRI image input part 13 may provide at least one parametric MRI image to the cancer detection model learning part 11. Here, the at least one parametric MRI image is an image reconstructed by applying various parameters to an MRI image, and may include a T2 (T2-weighted) image, an ADC (apparent diffusion coefficients) image, and a DWI (diffusion-weighted imaging) image, and the like.

The parametric MRI image input part 13 may receive original parametric MRI images 201 and 202 (refer to FIG. 2a), and may detect parametric MRI images obtained by extracting a prostate region from the original parametric MRI images 201 and 202, that is, the parametric MRI images 203 and 204 of the prostate region. In addition, the parametric MRI image input part 13 may provide the parametric MRI images 203 and 204 of the prostate region to the cancer detection model learning part 11.

The parametric MRI image input part 13 may display a screen 200 (refer to FIG. 2b) providing the parametric MRI images 203 and 204 of the prostate region on a display.

Meanwhile, the prostate of a user (or patient) may be excised, and a pathological image in which the region having the cancer tissue present therein is visualized from the excised prostate may be composed, wherein the labeling reference information providing part 15 may provide an environment in which the input of such a pathological image may be received. In addition, the labeling reference information providing part 15 may display the received pathology image 205 through one region of the screen 200.

In addition, the labeling processing part 17 may provide a user interface 210 capable of performing labeling on one region of the screen that displays: the parametric MRI images 203 and 204 of the prostate region provided by the parametric MRI image input part 13; and a pathological image 205 provided by the labeling reference information providing part 15.

The user interface 210 may include at least one parametric MRI image 211 (e.g., T2 image). In addition, the user interface 210 may be connected to an external input device such as a mouse device, a digitizer device, a touch screen device, and the like, and may include a predetermined indicator 212 output to the region designated by the external input device. In addition, the labeling processing part 17 may set a predetermined region, which is selected through the indicator 212, as a prostate cancer region. In addition, the user interface 210 may include a labeling indicator 213 displaying the corresponding region set as the prostate cancer region.

When the prostate cancer region is set through the user interface 210, the labeling processing part 17 provides the labeled region to the cancer detection model learning part 11. Accordingly, the cancer detection model learning part 11 may learn the prostate cancer detection model by inputting the parametric MRI images 203 and 204 of the prostate region and outputting the labeled region.

Furthermore, an MRI image may include various parameters, wherein since a T2 image or an ADC image is composed of a two-dimensional image, it may be difficult to check cancer tissue present in a region not displayed on the image itself.

Meanwhile, among images obtained on the basis of MRI, since a DWI (Diffusion-weighted imaging) image may represent information included in an MRI image as the information in which water molecules contained in the tissue diffuse in a specific direction, the information that is not displayed in the T2 image or the ADC image is able to be represented. In consideration of this fact, a parametric MRI image input by the parametric MRI image input part 13 may include a DWI image. Likewise, the parametric MRI image input by the parametric MRI image input part 13 may further include a DCE (dynamic contrast enhanced)-MRI image.

In addition, the labeling reference information providing part 15 may check DCE (dynamic contrast enhanced) signal information and may also display the DCE signal information 207 through one region of the screen 200. The DCE signal information 207 is the information of checking the brightness of a corresponding organ, and may be information of selecting a predetermined region from an image obtained on the basis of MRI and representing the brightness information on the selected region. Accordingly, the labeling reference information providing part 15 interlocks with the labeling processing part 17 to check the selected region, and may display the DCE signal information 207 corresponding thereto.

As another example, the labeling reference information providing part 15 may sequentially provide a pathology image 205, a DWI image 206, and DCE signal information 207.

In addition, as reference information, the labeling reference information providing part 15 may provide a T1 contrast image, a T2 contrast image, a PET (positron emission tomography) image, a SPECT (single photon emission computed tomography) image, a DSA (digital subtraction angiography) image, and the like.

The labeling reference information providing part 15 provides a pathology image 205, and may provide a DWI image 206 when the labeling processing part 17 performs a labeling process based on the pathology image 205. Thereafter, when the labeling processing part 17 completes the labeling process based on the DWI image 206, the DCE signal information 207 may be provided.

More specifically, as described above, the labeling reference information providing part 15 provides the parametric MRI images 203 and 204 and pathological image 205 of the prostate region through a first screen 220 (refer to FIG. 2c), and the labeling processing part 17 sets the region selected through a first user interface 230 as a cancer region, so that the labeling process based on the pathology image 205 may be performed.

In addition, the cancer detection model learning part 11 may learn a cancer detection model 100 by inputting the parametric MRI images 203 and 204 of the prostate region, and outputting the region labeled on the basis of the pathology image 205.

Furthermore, since the diagnosis region such as the prostate region is composed in a three-dimensional shape, detecting the characteristics in which an injury appears in a three-dimensional structure of the diagnosis region may improve the performance of the cancer detection model 100. In addition, when changes within the diagnosis region, for example, the diffusion of water in the tissue, the increase in contrast medium, and the like, are used as diagnostic indicators, a more accurate diagnosis becomes possible. In consideration of the above description, the parametric MRI image input part 13 may input information of DWI, DCE, and the like, wherein the information may be constructed and input in the moving image format, so as to visualize the three-dimensional structure of the diagnosis region or the changes in the diagnosis region. Corresponding to this way, the cancer detection model learning part 11 may perform learning of the cancer detection model 100 by using both the parametric MRI image in the still image format and the parametric MRI image in the moving image format. The operation of the cancer detection model learning part 11 to learn the cancer detection model 100 will be described in detail through the following FIGS. 3, 4, and 7, and related descriptions.

Figure 2A:
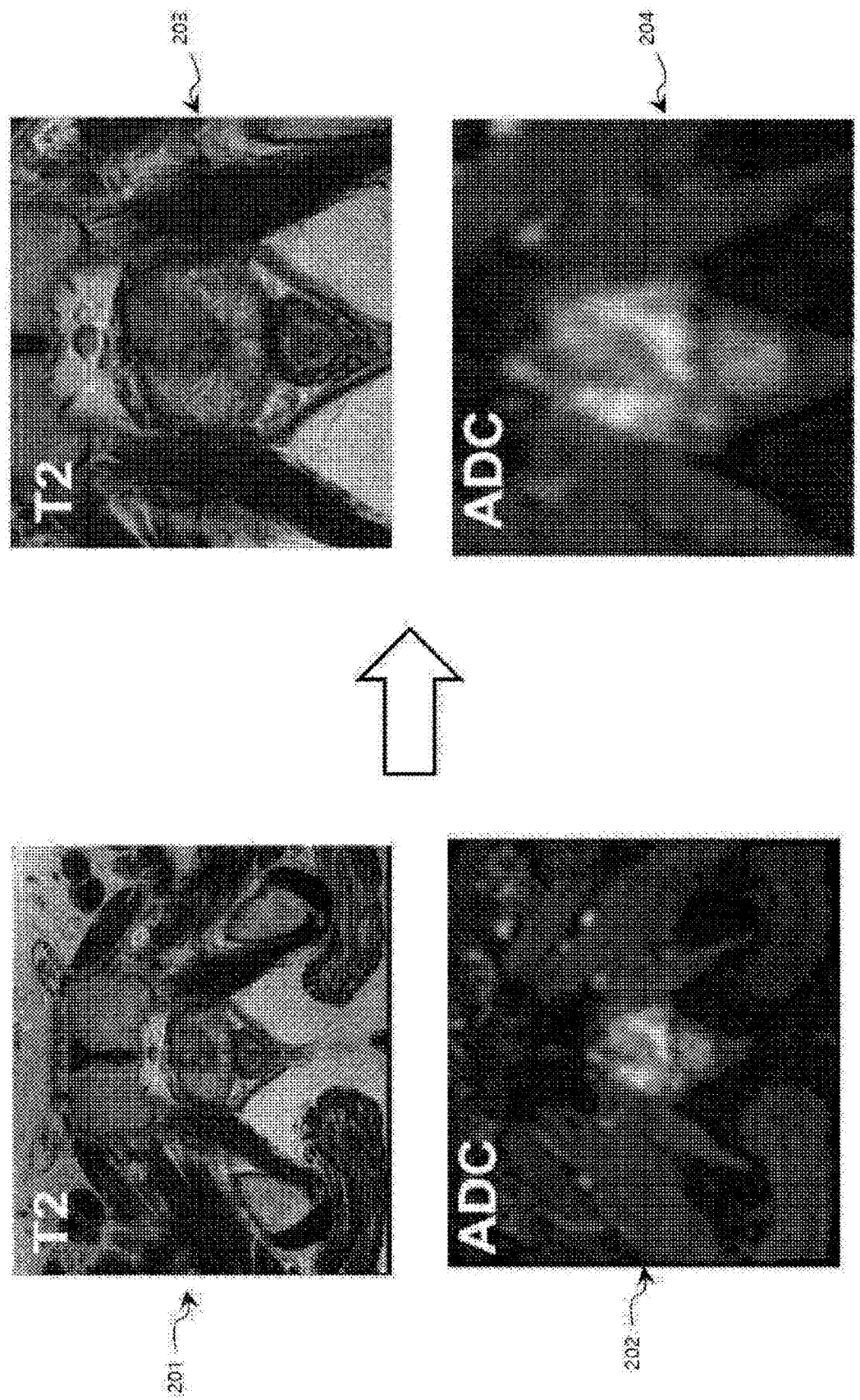
FIGS. 2a to 2g are views showing information processed by an operation of the deep learning model learning device according to the exemplary embodiment of the present disclosure.
Figure 2B:
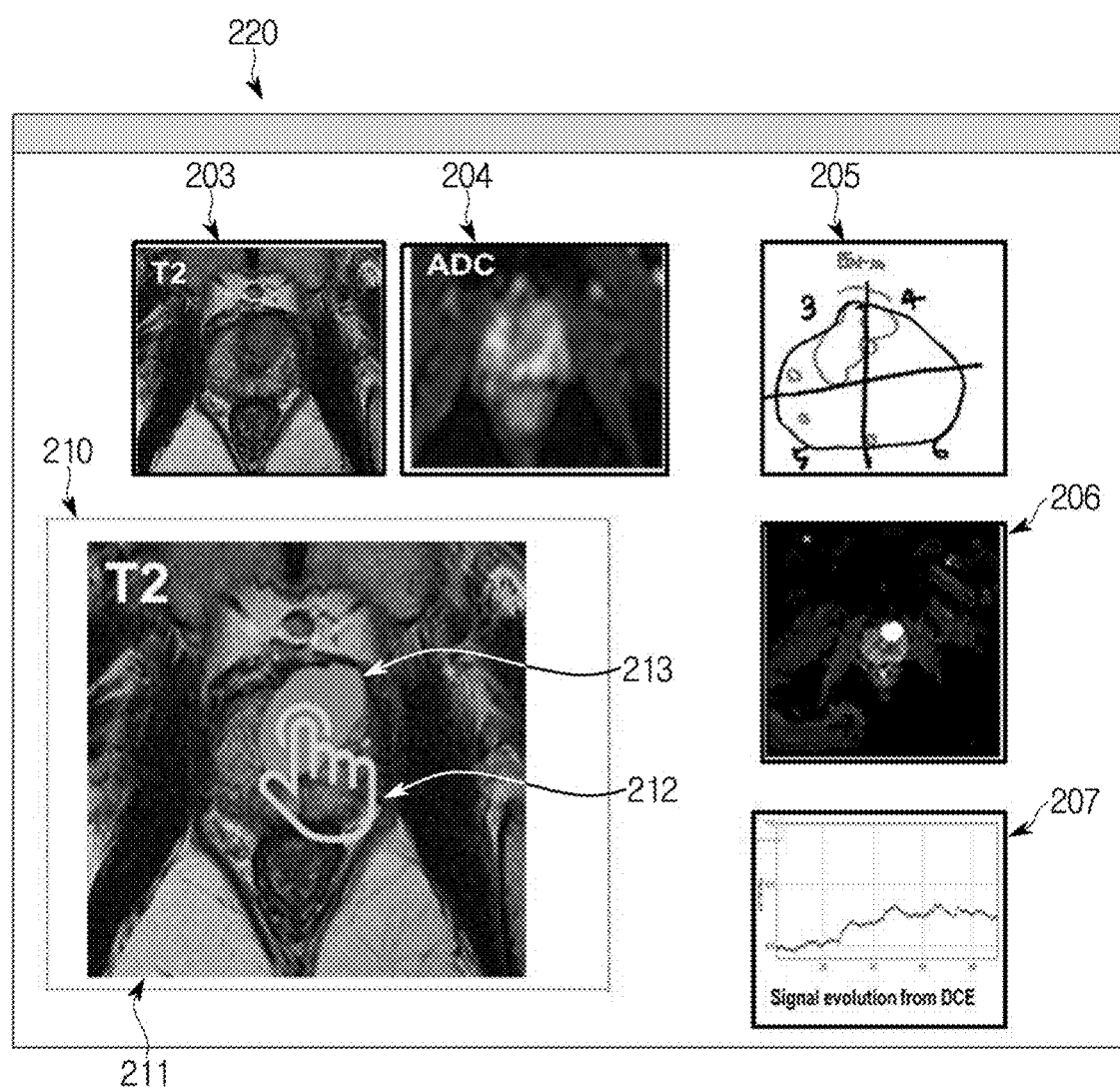
Figure 2C:
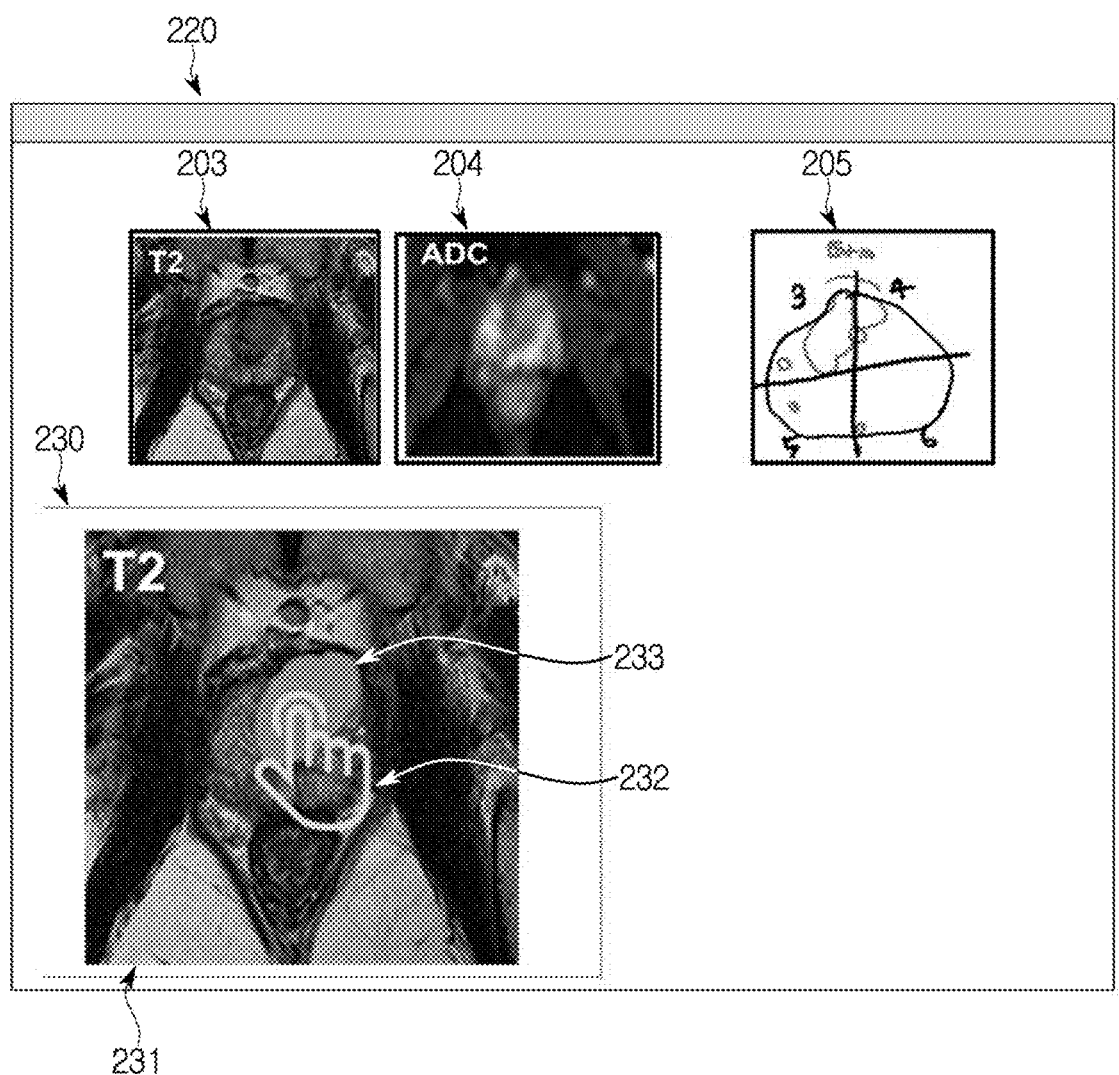
Figure 2D:
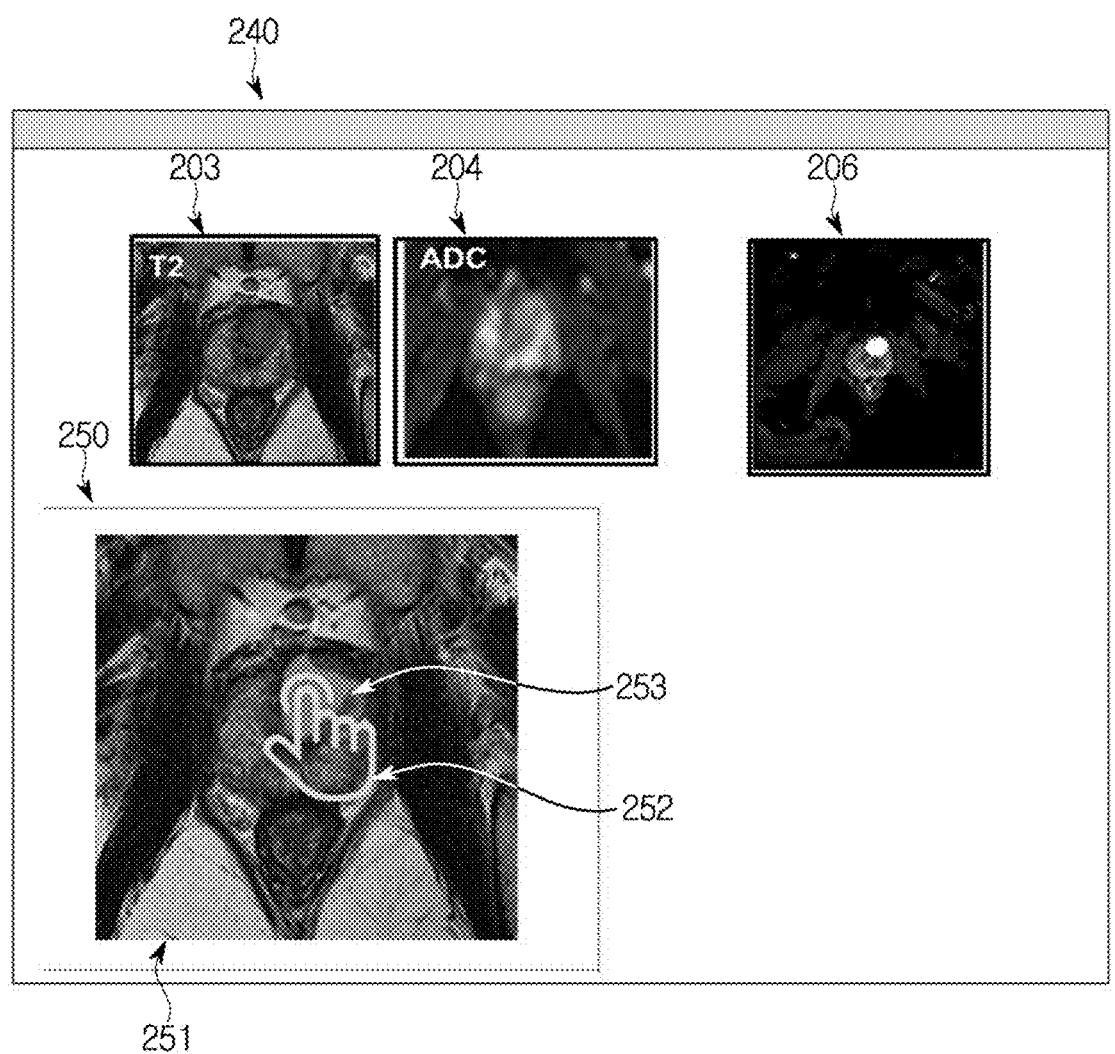

Thereafter, the labeling reference information providing part 15 may display the parametric MRI images 203 and 204 and DWI image 206 of the prostate region through a second screen 240 (refer to FIG. 2d). In addition, the labeling processing part 17 may provide a second user interface 250 capable of performing labeling in one region of the screen 240 displaying the parametric MRI images 203 and 204 of the prostate region provided by the parametric MRI image input part 13 and the DWI image 206 provided by the labeling reference information providing part 15. Here, similar to the first user interface 230 described above, the second user interface 250 may include at least one parametric MRI image 251 (e.g., T2 image), an indicator 252, and a labeling indicator 253.

In such an environment, the labeling processing part 17 may perform the labeling process based on the DWI image 206 by setting the region selected through the second user interface 250 as a prostate cancer region. In addition, the cancer detection model learning part 11 may learn the prostate cancer detection model by inputting the parametric MRI images 203 and 204 of the prostate region and outputting the region labeled on the basis of the DWI image 206.

Additionally, the cancer detection model learning part 11 may process the prostate cancer region, which is labeled on the basis of the pathological image 205, as an input.

Figure 2E:
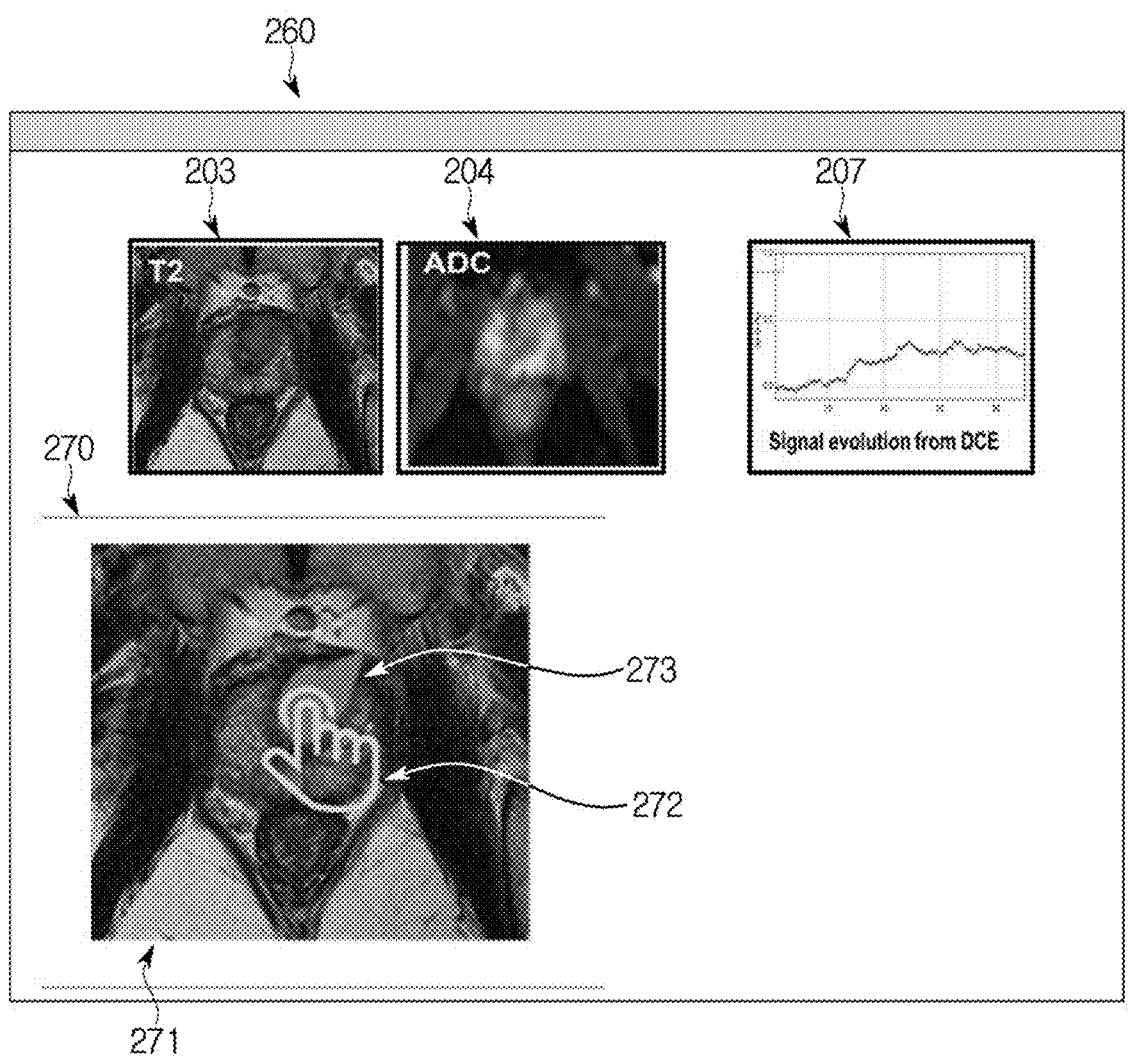

In addition, the labeling reference information providing part 15 may display the parametric MRI images 203 and 204 and DCE signal information 207 of the prostate region through a third screen 260 (refer to FIG. 2e). In addition, the labeling processing part 17 may provide a third user interface 270 capable of performing labeling in one region of the screen 260 displaying the parametric MRI images 203 and 204 of the prostate region provided by the parametric MRI image input part 13 and the DCE signal information 207 provided by the labeling reference information providing part 15. Here, similar to the first user interface 230 described above, the third user interface 270 may include at least one parametric MRI image 271 (e.g., T2 image), an indicator 272, and a labeling indicator 273.

In such an environment, the labeling processing part 17 may perform the labeling process based on the DCE signal information 207 by setting the region selected through the third user interface 270 as a prostate cancer region. In addition, the cancer detection model learning part 11 may learn the prostate cancer detection model by inputting the parametric MRI images 203 and 204 of the prostate region and outputting the region labeled on the basis of the DCE signal information 207.

Additionally, the cancer detection model learning part 11 may process a prostate cancer region, which is labeled on the basis of the DWI image 206, as an input.

In the exemplary embodiment of the present disclosure, it is exemplified that the labeling reference information providing part 15 provides the reference information in the order of the pathology image 205, the DWI image 206, and the DCE signal information 207, but the present disclosure is not limited thereto. The order in which the labeling reference information providing part 15 provides the reference information may be variously changed.

In addition, in the exemplary embodiment of the present disclosure, the reference information provided by the labeling reference information providing part 15 is exemplified as the pathological image 205, the DWI image 206, the DCE signal information 207, and the like, but the present disclosure is not limited thereto. The reference information provided by the labeling reference information providing part 15 may be varied by those skilled in the art of the present disclosure.

In addition, in the exemplary embodiment of the present disclosure, it is exemplified that the cancer detection model learning part 11 learns the deep learning model by using the at least one parametric MRI image as a basic input. It is apparent that the embodiment of present disclosure is not limited thereto, and may be variously changed. For example, the cancer detection model learning part 11 may use at least one of the DWI image and DCE signal information as the input. In other words, when learning the deep learning model by using the labeling information based on the at least one parametric MRI image and the DWI image, the cancer detection model learning part 11 may use the DWI image together with the at least one parametric MRI image, as an input. Similarly, when learning the deep learning model by using the labeling information based on the at least one parametric MRI image and DCE signal information, the cancer detection model learning part 11 may use the DCE signal information together with the at least one parametric MRI image, as an input.

Additionally, when learning the deep learning model by using the labeling information based on at least one parametric MRI image and pathology information, the cancer detection model learning part 11 may use the pathology information together with the at least one parametric MRI image, as an input.

In the exemplary embodiment of the present disclosure, although the diagnosis region is exemplified as the prostate region, and the region where cancer is present is exemplified as the prostate cancer region, the present disclosure is not limited thereto, and may apparently be applied to various different diagnosis regions.

Figure 2F:
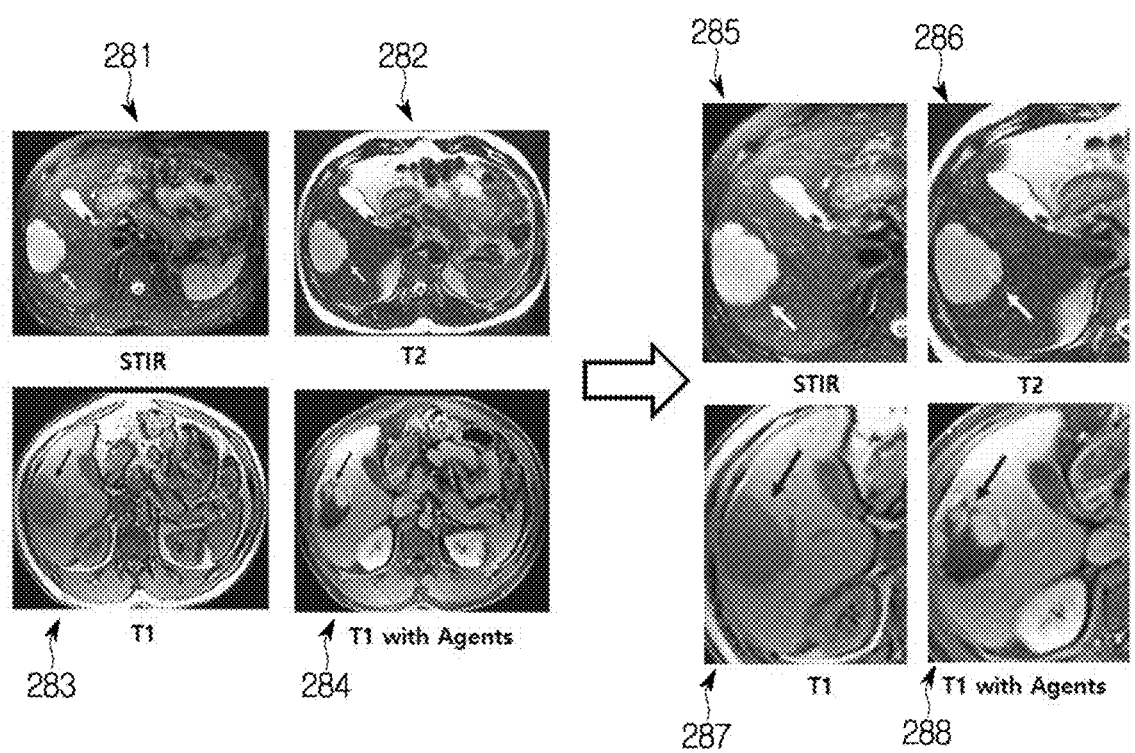
Figure 2G:
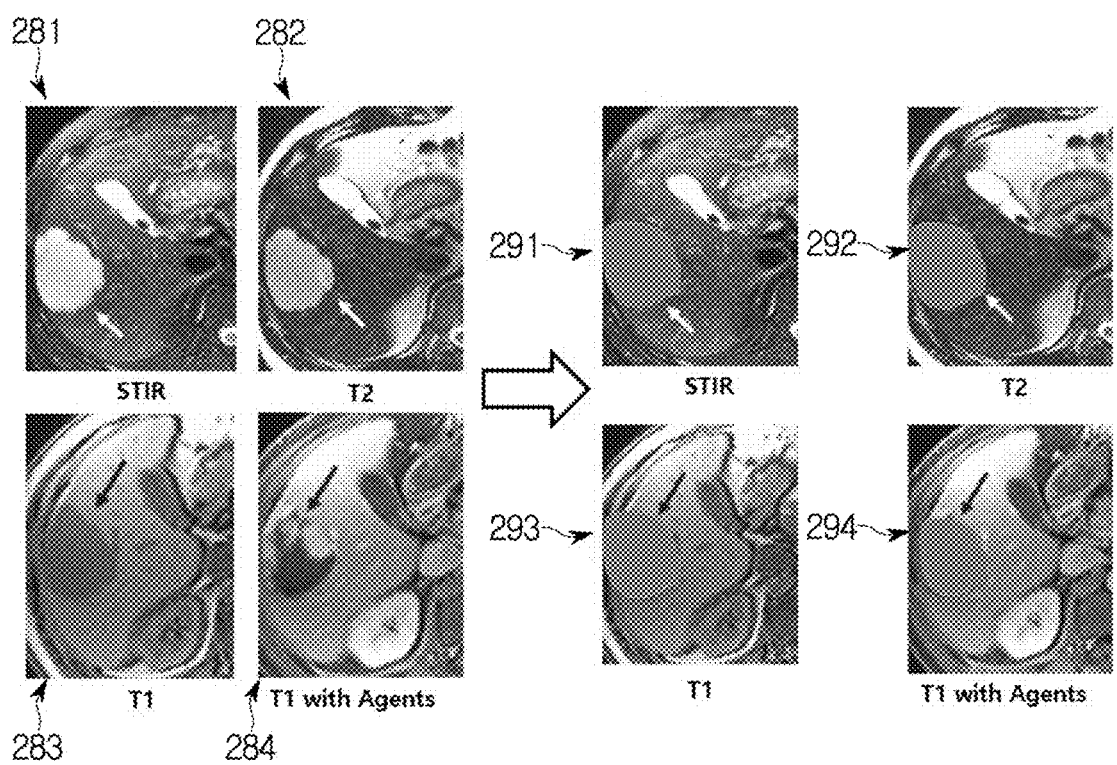

For example, as illustrated in FIGS. 2f and 2g, the diagnosis region may be applied as a region in which the liver is present, and the region in which cancer is present may be applied as a liver cancer region. Accordingly, the cancer detection model learning part 11 may operate in consideration of the region where the liver is present or the liver cancer region.

Specifically, as for at least one parametric MRI image, the parametric MRI image input part 13 may detect and provide a parametric MRI image extracting a liver region from an original parametric MRI images 281, 282, 283, and 284 (refer to FIG. 2f), such as a STIR (short TI inversion recovery) image, a T1 (T1-weighted) image, and a T1 with agents image, that is, the parametric MRI images 285, 286, 287, and 288 of the liver region.

The labeling processing part 17 may perform the labeling process based on the reference information by setting the region, which is selected on the basis of reference information (e.g., T1 contrast image, T2 contrast image, etc.) provided by the labeling reference information providing part 15, as the liver cancer region. In addition, the cancer detection model learning part 11 may learn the liver cancer detection model by inputting the parametric MRI images 285, 286, 287, and 288 of the liver region and outputting the region 291, 292, 293, and 294 (refer to FIG. 2g) labeled on the basis of the reference information.

As another example, a diagnosis region may be applied as the region where the brain is present, and the region where cancer is present may be applied as a brain cancer region. Accordingly, the cancer detection model learning part 11 may operate in consideration of the region where the brain is present or the brain cancer region. In other words, as for at least one parametric MRI image, the parametric MRI image input part 13 may detect and provide a parametric MRI image extracting the brain region from the original parametric MRI image such as the TI image, the T2 image, and the FLAIR image, that is, the parametric MRI image of the brain region. In addition, the labeling processing part 17 may perform the labeling process based on the reference information by setting a region, which is selected on the basis of reference information (e.g., information of FDG-PET, SPECT, etc.) provided by the labeling reference information providing part 15, as the brain cancer region. Through such an operation, the cancer detection model learning part 11 may learn the brain cancer detection model by inputting the parametric MRI image of the brain region and outputting the region labeled on the basis of the reference information.

Figure 3:
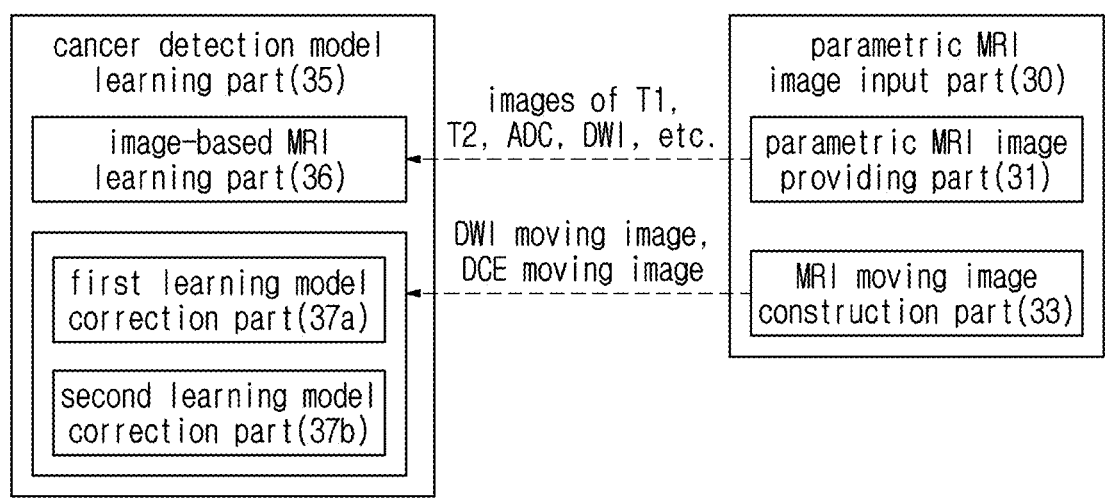
FIG. 3 is a block diagram showing a detailed configuration of a parametric MRI image input part and a cancer detection model learning part according to the exemplary embodiment of the present disclosure.
Figure 4:
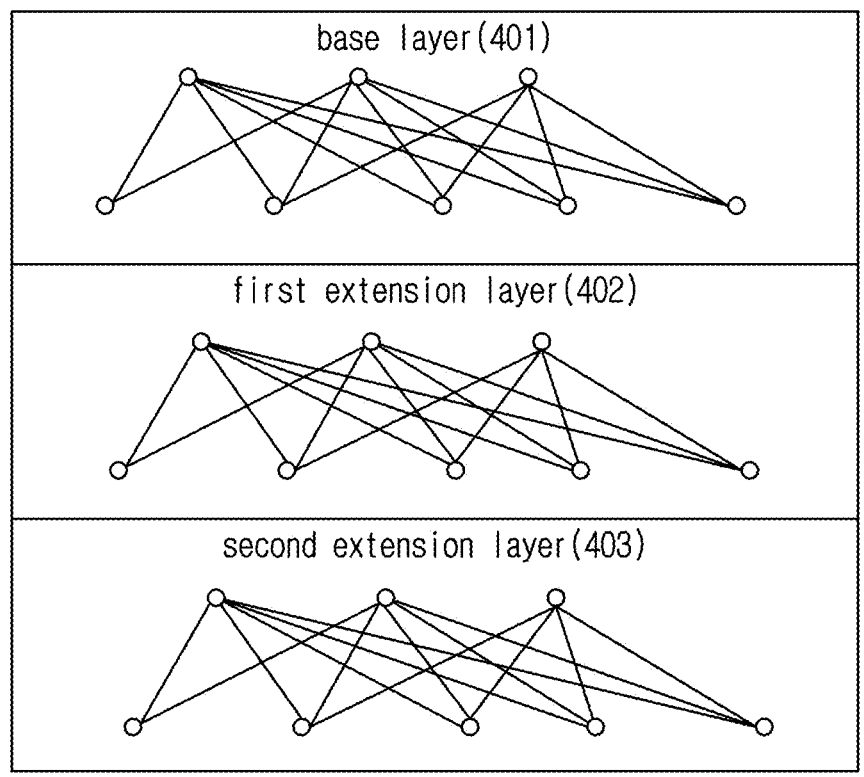
FIG. 4 is a view showing a detail structure of a cancer detection model according to the exemplary embodiment of the present disclosure.

FIG. 3 is a block diagram showing a detailed configuration of a parametric MRI image input part and a cancer detection model learning part, which are provided in the deep learning model learning device according to the exemplary embodiment of the present disclosure.

Referring to FIG. 3, the parametric MRI image input part 30 may include a parametric MRI image providing part 31 and an MRI moving image construction part 33. The parametric MRI image providing part 31 may check a parametric MRI image in the still image format, for example, the images of T1, T2, ADC, DWI, and the like to provide the parametric MRI image to the cancer detection model learning part 35. In addition, the MRI moving image construction part 33 may configure and provide the moving image format parametric MRI image (e.g., images of DWI, DCE, etc.) where a temporal change occurs. Specifically, at each predetermined time unit, the Mill moving image construction part 33 continuously photographs DWI images indicating an arranged state of cells by using the fine motility of water molecules in the tissue, and combines the continuously photographed DWI images, thereby composing the DWI moving image. As another example, at each predetermined time unit, the Mill moving image construction part 33 continuously photographs DCE images evaluating a blood flow state of the tissue by measuring a change in the contrast enhancement intensity after injection of a contrast agent, and combines the continuously photographed DCE images, thereby composing the DCE moving image.

The cancer detection model learning part 35 may include an image-based Mill learning part 36 and a learning model correction part 37. First, the image-based Mill learning part 36 may perform learning on a cancer detection model by performing learning on a parametric Mill in the image format. In this case, the image-based MRI learning part 36 applies the convolutional neural network (CNN) technique or the pooling technique to the at least one parametric MRI image provided by the parametric MRI image providing part 31, so as to construct a base layer of the cancer detection model. In this case, the parametric MRI image in use may be variously changed. After the base layer of the cancer detection model is constructed through the image-based MRI learning part 36, the learning model correction part 37 uses the MRI moving image provided by the MRI moving image construction part 33 to construct an extension layer of the cancer detection model, thereby being able to perform correction for the cancer detection model. For example, the learning model correction part 37 may detect spatial characteristics of each frame provided in the MRI moving image, and then construct the extension layer so as to detect characteristics according to the temporal arrangement of each frame. In this case, the spatial characteristics of each frame may be constructed on the basis of the convolutional neural network (CNN) technique or the pooling technique, and the characteristics according to the temporal arrangement of each frame may be constructed on the basis of a learning method of the recurrent neural network (RNN).

Furthermore, the learning model correction part 37 may be configured to construct a plurality of extension layers step by step. For example, the learning model correction part 37 may include a first correction part 37a and a second correction part 37b. The first correction part 37a is configured to construct a first extension layer of the cancer detection model by using a first MRI moving image, and the second correction part 37*b* is configured to construct a second extension layer of the cancer detection model by using a second MRI moving image. Accordingly, the cancer detection model may be configured such that a base layer 401, a first extension layer 402, and a second extension layer 403 are connected one after another in series. Furthermore, the first MRI moving image and the second MRI moving image may be different types of MRI moving images, respectively. For example, the first MRI moving image may be a DWI moving image constructed by combining successively photographed DWI images, and the second MRI moving image may be a DCE moving image constructed by combining successively photographed DCE images.

Figure 5:
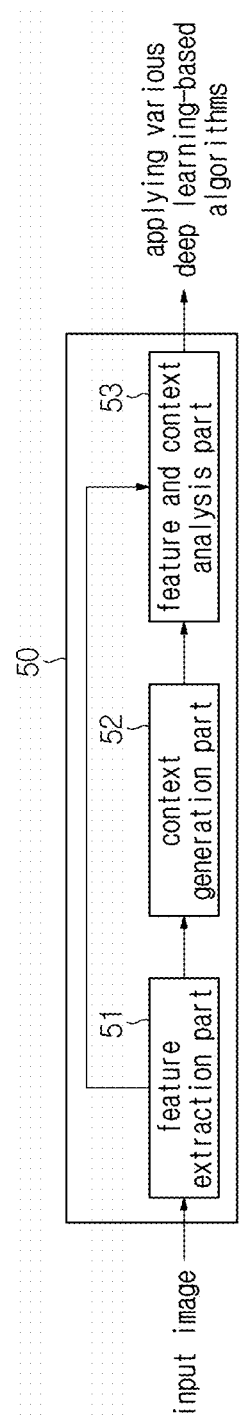
FIG. 5 is a view showing a detailed configuration of the image-based MRI learning part of FIG. 3.

FIG. 5 is a view showing a detailed configuration of the image-based MRI learning part of FIG. 3.

Referring to FIG. 5, the cancer detection model learning part 50 may include a feature extraction part 51, a context generation part 52, and a feature and context analysis part 53. However, this view is only showing some components necessary for describing the present exemplary embodiment, and components included in the cancer detection model learning part 50 are not limited to the above-described examples.

The cancer detection model learning part 50 extracts features of the analysis target image, generates context information on the basis of the extracted features, and analyzes the analysis target image on the basis of the extracted features and the generated context information. For example, the cancer detection model learning part 50 may classify images or find a location of an object of interest by using the extracted features and generated context information.

The input image of the cancer detection model learning part 50 may be at least one parametric MRI image. The at least one parametric MRI image (e.g., T2 image, ADC image, etc.) may be a raw image reconstructed on the basis of a predetermined parameter from the Mill, or may be an arbitrary format image for storing or transmitting the raw image.

The feature extraction part 51 may analyze an input image to extract a feature of the image. For example, the feature may be a local feature for each region of the image. The feature extraction part 51 according to the exemplary embodiment may extract features of the input image by using the general convolutional neural network (CNN) technique or the pooling technique. The pooling technique may include at least one of a max pooling technique and an average pooling technique. However, the pooling technique referred to in the present disclosure is not limited to the max pooling technique or the average pooling technique, but includes any technique for obtaining a representative value of an image region having a predetermined size. For example, the representative value used in the pooling technique may be at least one of a variance value, a standard deviation value, a mean value, a most frequent value, a minimum value, a weighted average value, and the like, in addition to a maximum value and an average value.

The convolutional neural network of the present disclosure may be used to extract "features" such as borders, line colors, and the like from input data (i.e., image), and may include a plurality of layers. Each layer may generate output data by receiving the input data and processing the input data of a corresponding layer. In the convolutional neural network, a feature map is generated by convolving an input image or an input feature map with a filter kernel and may be output as the output data. The initial layers of the convolutional neural network may be operated to extract low-level features such as edges or gradients from the input. The next layers of the neural network may gradually extract more complex features such as eyes, nose, etc.

The convolutional neural network may include a convolutional layer in which a convolution operation is performed, as well as a pooling layer in which a pooling operation is performed. The pooling technique is a technique used to reduce a spatial size of data in the pooling layer. Specifically, the pooling technique includes: a max pooling technique that selects a maximum value in a corresponding region; and an average pooling technique that selects an average value of the corresponding region, wherein the max pooling technique is generally used in the image recognition field. In the pooling technique, generally, a pooling window size and an interval (i.e., stride) are set to have the same value. Here, the stride relates to adjusting an interval for a filter to move when applying the filter to input data. The stride means the interval where the filter moves, and the stride may also be used to adjust a size of output data. A detailed operation of the pooling technique will be described later with reference to FIG. 6.

The feature extraction part 51 according to the exemplary embodiment of the present disclosure may apply filtering to an analysis target image as pre-processing for extracting a feature of the analysis target image. The filtering may be fast Fourier transform (FFT), histogram equalization, motion artifact removal or noise removal, etc. However, the filtering of the present disclosure is not limited to the above-described methods, and may include any type of filtering capable of improving image quality.

The context generation part 52 may generate context information of an input image (i.e., analysis target image) by using the features of the input image extracted from the feature extraction part 51. For example, the context information may be a representative value representing the entire or partial region of the analysis target image. In addition, the context information may be global context information of the input image. The context generation part 52 according to the exemplary embodiment may generate context information by applying the features extracted from the feature extraction part 51 using the convolutional neural network technique or the pooling technique. The pooling technique may be, for example, the average pooling technique.

The feature and context analysis part 53 may analyze an image on the basis of a feature extracted by the feature extraction part 51 and context information generated by the context generation part 52. The feature and context analysis part 53 according to the exemplary embodiment uses the local feature of each region of the image extracted by the feature extraction part 51 and the global context reconstructed in the context generation part 52 together in such a way as to concatenate the local feature and the global context, thereby being able to classify the input image or find the location of the object of interest included in the input image. Since the information at a specific two-dimensional position in the input image includes not only local feature information but also global context information, the feature and context analysis part 53 uses this information, so that more accurate recognition or classification becomes possible for input images that have different actual content but similar local feature information.

As described above, the invention according to the exemplary embodiment of the present disclosure enables more accurate and efficient learning and image analysis to be performed by using the global context information as well as the local features used by a general convolutional neural network technique. From this point of view, the invention according to the present disclosure may be referred to as a "deep neural network through context analysis".

Figure 6:
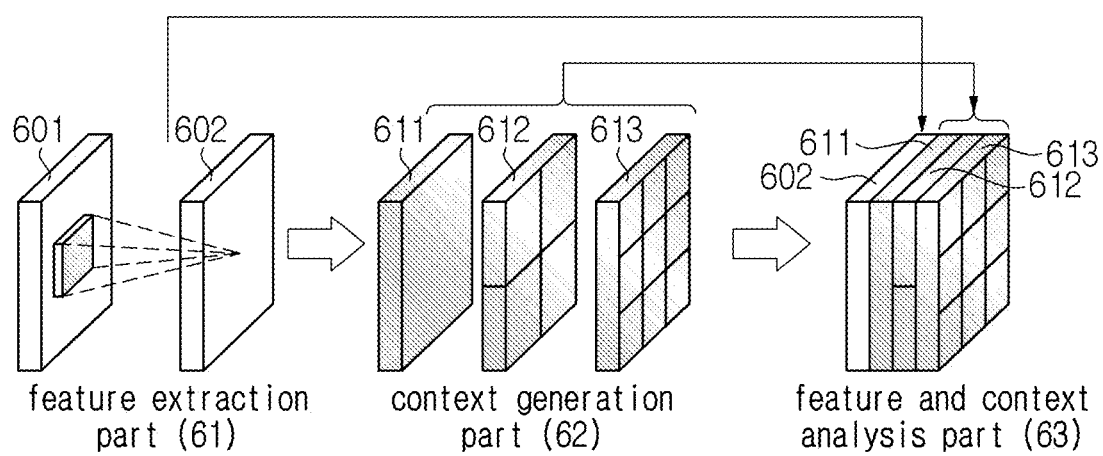
FIG. 6 is a view showing a process of generating and analyzing context information of an image according to the exemplary embodiment of the present disclosure.

FIG. 6 is a view showing a process of generating and analyzing context information of an image according to the exemplary embodiment of the present disclosure.

Referring to FIG. 6, the feature extraction part 51 uses an input image 601 to extract a feature from the input image 601, and may generate a feature image 602 including information of the extracted feature. The extracted feature may be the feature of a local region of the input image. The input image 601 may include an input image of an image analysis device or a feature map of each layer in the convolutional neural network model. In addition, the feature image 602 may include a feature map and/or a feature vector obtained by applying the convolutional neural network technique and/or pooling technique to the input image 601.

The context generation part 52 may generate context information by applying the convolutional neural network technique and/or pooling technique to the feature image 602 extracted by the feature extraction part 51. For example, by variously adjusting the pooling stride, the context generation part 52 may generate context information of images having various scales, such as an entire region, a quadrant region, and a nine equal part region. Referring to FIG. 6, the context generation part 52 may obtain images, including: an entire context information image 611 including context information for a full-sized image; a quadrant context information image 612 including context information for a quadrant image having a size obtained by dividing the entire image into quarters; and a nine equal part context information image 613 including context information for a nine equal part image having a size obtained by dividing the entire image into nine equal parts.

The feature and context analysis part 53 may more accurately analyze a specific region of the analysis target image by using both the feature image 602 and the context information images 611, 612, and 613.

For example, when an image including a benign tumor having a form similar to that of prostate cancer is the input image, it is not possible to accurately determine whether an identified object obtained from the feature image 602 including a local feature extracted by the feature extraction part 51 is prostate cancer or a benign tumor. That is, the feature extraction part 51 may recognize a shape of the object on the basis of the local feature, but there are cases in which it is not possible to accurately identify and classify the object only with the shape of the object.

The context generation part 52 according to the exemplary embodiment of the present disclosure generates context information 411, 412, and 413 on the basis of the analysis target image or the feature image 602, so as to more accurately identify and classify an object.

The feature and context analysis part 53 according to the exemplary embodiment of the present disclosure uses the context information, so as to identify an object having the shape of the prostate cancer or benign tumor and classify the object as "prostate cancer".

In the exemplary embodiment described with reference to FIG. 6, it has been described that context information for the entire image, context information for a quadrant image, and context information for a nine equal part image are generated and utilized, but the size of an image for extracting the context information is not limited thereto. For example, context information for an image having a size other than the above-described image may be generated and utilized.

Figure 7:
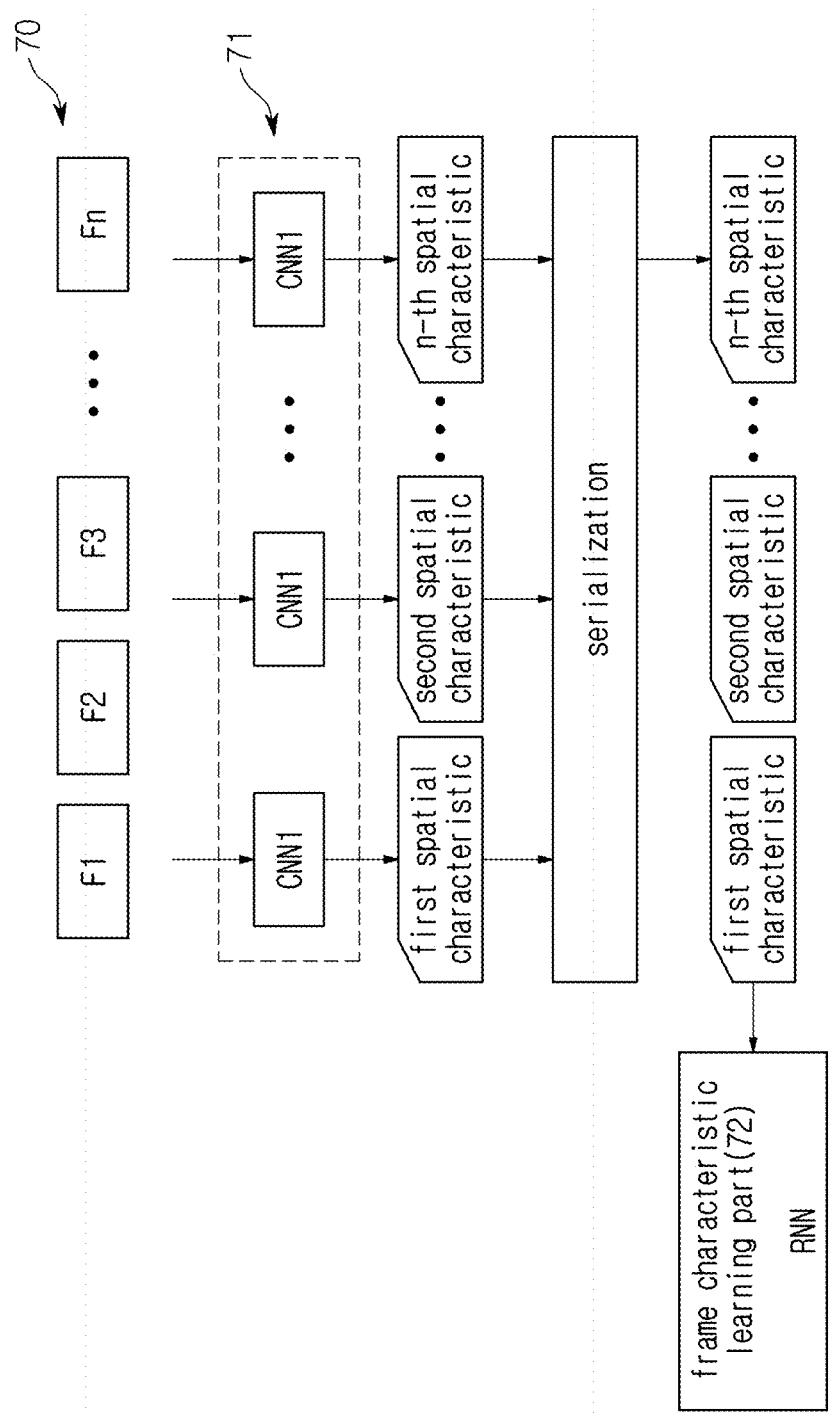
FIG. 7 is a view showing a detailed configuration of the learning model correction part of FIG. 3.

FIG. 7 is a view showing a detailed configuration of the learning model correction part of FIG. 3.

The learning model correction part 70 may include a spatial characteristic learning part 71 and a frame characteristic learning part 72.

The spatial characteristic learning part 71 may construct a spatial characteristic learning model by performing learning on each of the image frames F1, F2, . . . , and Fn included in the MRI moving image, and preferably, may construct the spatial characteristic learning model on the basis of a learning method of the convolutional neural network (CNN).

When constructing the spatial characteristic learning model of the spatial characteristic learning part 71, information on the time or arrangement order corresponding to the image frames F1, F2, . . . , and Fn may be considered. For example, the spatial characteristic learning model may be provided with the CNN corresponding to the number of image frames F1, F2, . . . , and Fn included in an MRI moving image, and the spatial characteristic learning part 71 may be configured such that a first image frame F1 is transmitted as an input of a first CNN, a second image frame F2 is transmitted as an input of a second CNN, and an n-th image frame Fn is transmitted as an input of an n-th CNN.

Corresponding to the above description, a plurality of CNNs provided in the spatial characteristic learning model 71 may output a plurality of spatial characteristics corresponding to each of a plurality of image frames F1, F2, . . . , and Fn, and the spatial characteristic learning part 71 may sequentially arrange the plurality of spatial characteristics described above to constitute sequential data. In this case, the spatial characteristic learning part 71 may constitute the sequential data in consideration of information on the time or arrangement order corresponding to the image frames F1, F2, . . . , and Fn.

Meanwhile, the frame characteristic learning part 72 may receive the plurality of spatial characteristics composed of the sequential data and perform learning to detect the characteristics (i.e., frame characteristics) regarding a relationship between the image frames. Preferably, the frame characteristic learning part 72 may construct a frame characteristic learning model on the basis of the learning method of the recurrent neural network (RNN).

The recurrent neural network (RNN) is applied as a deep learning technique that considers both current and past data at the same time, and in the recurrent neural network (RNN), the connection between units constituting an artificial neural network represents a neural network that constitutes a directed cycle. Furthermore, various methods may be used for a structure capable of constituting the recurrent neural network (RNN). For example, representative methods include: a fully recurrent network, a Hopfield network, an Elman Network, and an echo state network (ESN), a long short term memory network (LSTM), a bi-directional RNN, a continuous-time RNN (CTRNN), a hierarchical RNN, a secondary RNN, etc. In addition, as a method for training the recurrent neural network (RNN), a gradient descent method, a Hessian free optimization, a global optimization method, and the like may be used.

Meanwhile, since spatial characteristic information is the information extracted from the image frames F1, F2, . . . , and Fn included in the MRI moving image, the frame characteristic learning part 72 checks temporal information of the image frames F1, F2, . . . , and Fn included in the MRI moving image and may process the frame characteristic learning for the spatial characteristic information on the basis of the checked temporal information. The spatial characteristic information may be sequentially input to the frame characteristic learning model, and the frame characteristic learning model may sequentially output the frame characteristics 700-1, 700-2, . . . , and 700-*n*.

Figure 8:
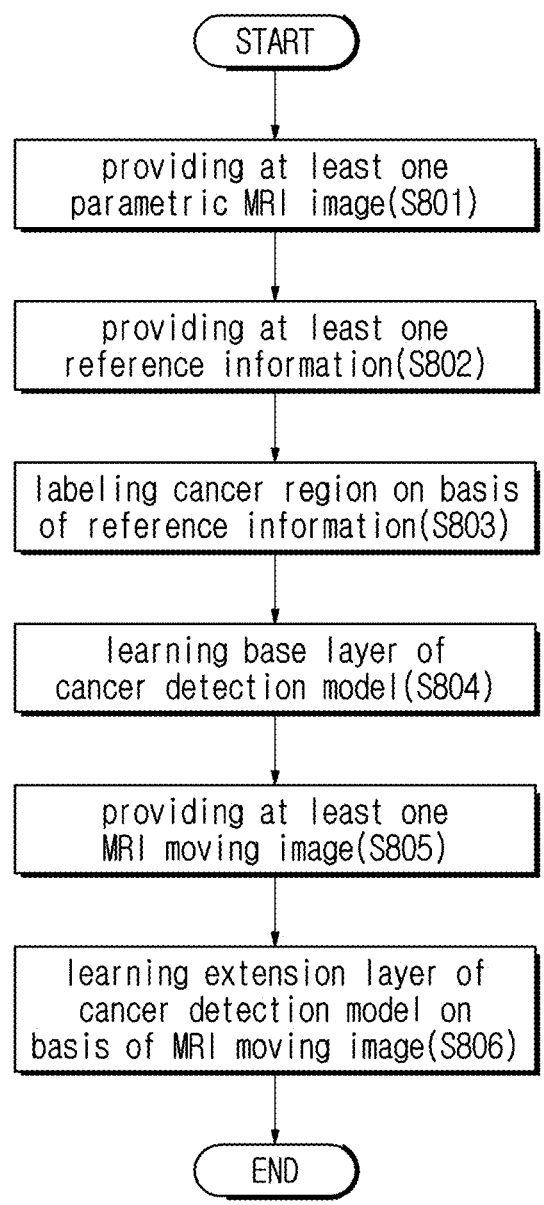
FIG. 8 is a flowchart showing a procedure of a deep learning model learning method according to a exemplary embodiment of the present disclosure.

FIG. 8 is a flowchart showing a procedure of the deep learning model learning method according to the exemplary embodiment of the present disclosure.

The deep learning model learning method according to the exemplary embodiment of the present disclosure may be performed by the above-described deep learning model learning device.

In step S801, a deep learning model learning device may provide at least one parametric MRI image. Images in which a user's body is photographed by a magnetic resonance imaging (MRI) device, that is, the MRI images may be applied with various parameters to reconstruct various images, and the image reconstructed by applying the predetermined parameter to the MRI image is indicated as the parametric MRI image. Here, at least one parametric MRI image may include: a T1 (T1-weighted) image, a T2 (T2-weighted) image, a T2* (T2 star) image, an ADC (apparent diffusion coefficients) image, a FLAIR (fluid attenuated inversion recovery) image, a STIR (short TI inversion recovery) image, a PWI (perfusion weighted image), etc.

Furthermore, the deep learning model learning device may learn a cancer detection model for various body organs or diagnosis regions provided in the body of a user (or patient), and at least one parametric MRI image may be selectively used on the basis of the characteristics of each of the body organ and diagnosis region, or the cancer region present in the body organ or diagnosis region. To this end, the deep learning model learning device may selectively input at least one parametric MRI image, which is corresponding to the body organ or diagnosis region, into the deep learning model.

For example, in a case where a body organ or diagnosis region is a prostate region, the deep learning model learning device may input a T2 (T2-weighted) image, an ADC (apparent diffusion coefficients) image, etc. As another example, in a case where a body organ or diagnosis region is a liver region, the deep learning model learning device may input a STIR image, a T1 image, a T1 with agents image, a T2 image, etc. As yet another example, in a case where a body organ or a diagnosis region is a brain region, the deep learning model learning device may input a T1 image, a T2 image, a FLAIR, etc.

Furthermore, the at least one parametric MRI image may be an image obtained by extracting a region corresponding to the diagnosis region. Specifically, the deep learning model learning device may receive original parametric MRI images 201 and 202 (refer to FIG. 2*a*), and may detect a parametric MRI image obtained by extracting the diagnosis region from the original parametric MRI images 201 and 202, that is, the parametric MRI images 203 and 204 of the diagnosis region. In addition, the deep learning model learning device may provide parametric MRI images 203 and 204 in the diagnosis region.

In this case, the deep learning model learning device may provide the parametric MRI images 203 and 204 in the diagnosis region as an input for learning the deep learning model. In addition, the deep learning model learning device may construct a screen 200 (refer to FIG. 2*b*) that provides the parametric MRI images 203 and 204 of the diagnosis region, so as to output the parametric MRI images 203 and 204 on a display and the like.

In step S802, the deep learning model learning device may provide information (hereinafter referred to as "reference information") that may be referred to designating a region where cancer is located in the parametric MRI images 203 and 204 of the diagnosis region.

For example, a diagnosis region of a user (or patient) may be excised, and a pathology image visualizing a region where cancer tissue is present may be constructed from the excised diagnosis region, and the deep learning model learning device may provide an environment in which such a pathology image may be input. In addition, the deep learning model learning device may display the received pathology image 205 through one region of the screen 200.

The MRI image may include various parameters, wherein since the T2 image or ADC image is composed of a two-dimensional image, it may be difficult to check cancer tissue present in a region not displayed on the image itself. Meanwhile, among images obtained on the basis of MRI, since a DWI (diffusion-weighted imaging) image is able to represent information included in an MRI image as the information in which water molecules contained in the tissue diffuse in a specific direction, the information that is not displayed in the T2 image or the ADC image may be represented. In consideration of the above description, the deep learning model learning device may additionally display the DWI image 205 through one region of the screen 200.

Furthermore, the deep learning model learning device may check DCE (dynamic contrast enhanced) signal information, and may additionally display the DCE signal information 207 through one region of the screen 200. The DCE signal information 207 is the information of checking the brightness of a corresponding organ, and may be information of selecting a predetermined region from an image obtained on the basis of MRI and representing the brightness information on the selected region. Accordingly, the deep learning model learning device checks the region selected by the user through a user interface, and may display the DCE signal information 207 corresponding thereto.

Furthermore, according to the characteristics of each body organ or each diagnosis region, or a cancer region present in the body organ or diagnosis region, information that may be used as reference information for labeling may be variously changed. Accordingly, the deep learning model learning device may selectively provide the reference information that contributes to the labeling processing of the cancer region on the basis of the characteristics of each body organ or each diagnosis region, or the cancer region present in the body organ or diagnosis region.

For example, in the case where a body organ or a diagnosis region is a prostate region, the deep learning model learning device may provide a T1 contrast image, a T2 contrast image, a PET (positron emission tomography) image, a SPECT (single photon emission computed tomography) image, a DSA (digital subtraction angiography) image, and the like, as reference information. As another example, in the case where a body organ or a diagnosis region is a liver region, the deep learning model learning device may input a T1 contrast image, a T2 contrast image, etc. As yet another example, in the case where a body organ or a diagnosis region is a brain region, the deep learning model learning device may provide FDG-PET image, SPECT image, and the like, as reference information.

In step S803, the deep learning model learning device may provide a user interface 210 capable of performing labeling, while displaying reference information (i.e., pathology image 205, DWI image 206, DCE signal information 207, etc.) The user interface 210 may include at least one parametric MRI image (e.g., T2 image) 211. In addition, the user interface 210 may be connected to an external input device such as a mouse device, a digitizer device, a touch screen device, and the like, and may include a predetermined indicator 212 output to a region designated by the external input device. In addition, the deep learning model learning device may set a predetermined region selected through the indicator 212 as a cancer region, and the user interface 210 may include a labeling indicator 213 displaying the corresponding region set as the cancer region.

In step S804, when a cancer region is set through the user interface 210, the deep learning model learning device may perform learning on the base layer of the cancer detection model by inputting the parametric MRI images 203 and 204 of the prostate region and outputting the labeled region.

Thereafter, in step S805, the deep learning model learning device may provide at least one MRI moving image. In this case, the at least one MRI moving image may include: a DWI moving image constructed by continuously photographing DWI images at every predetermined time unit, the DWI images indicating the arranged state of cells by using the microscopic motility of water molecules in the tissue; and a DCE moving image constructed by continuously photographing DCE images at every predetermined time unit, the DCE images evaluating the blood flow in the tissue by measuring changes in the contrast enhancement intensity after injection of a contrast agent.

In step S806, the deep learning model learning device may perform learning on the at least one MRI moving image, so as to learn an extension layer of the cancer detection model. For example, the deep learning model learning device may construct a spatial characteristic learning model by performing learning on each of the image frames F1, F2, . . . , and Fn included in the MRI moving image, and preferably, may construct the spatial characteristic learning model on the basis of the learning method of the convolutional neural networks (CNN). In this case, the deep learning model learning device may consider information on the time or arrangement order corresponding to the image frames F1, F2, . . . , and Fn when constructing the spatial characteristic learning model. For example, the spatial characteristic learning model may be provided with the CNN corresponding to the number of image frames F1, F2, . . . , and Fn included in the MRI moving image, and the spatial characteristic learning part 71 may be configured such that a first image frame F1 is transmitted as an input of a first CNN, a second image frame F2 is transmitted as an input of a second CNN, and an n-th image frame Fn is transmitted as an input of an n-th CNN. Corresponding to the above description, the plurality of CNNs provided in the spatial characteristic learning model may output the plurality of spatial characteristics corresponding to each of the plurality of image frames F1, F2, . . . , and Fn, and the deep learning model learning device may sequentially arrange the plurality of spatial characteristics described above to construct sequential data. In this case, the deep learning model learning device may construct the sequential data in consideration of information on the time or arrangement order corresponding to the image frames F1, F2, . . . , and Fn. Meanwhile, the deep learning model learning device receives the plurality of spatial characteristics composed of the sequential data, and may perform learning to detect the characteristics (i.e., frame characteristics) regarding a relationship between image frames. Preferably, the deep learning model learning device may construct a frame characteristic learning model on the basis of the learning method of the recurrent neural network (RNN).

The recurrent neural network (RNN) serves as a deep learning technique that considers both current and past data at the same time, and in the recurrent neural network (RNN), a connection between units constituting the artificial neural network represents the neural network that constitutes the directed cycle. Furthermore, various methods may be used for the structure capable of constituting the recurrent neural network (RNN). For example, the representative methods include: a fully recurrent network, a Hopfield network, an Elman Network, and an echo state network (ESN), a long short term memory network (LSTM), a bi-directional RNN, a continuous-time RNN (CTRNN), a hierarchical RNN, a secondary RNN, etc. In addition, as a method for training the recurrent neural network (RNN), a gradient descent method, a Hessian free optimization, a global optimization method, and the like may be used.

Meanwhile, since the spatial characteristic information is the information extracted from the image frames F1, F2, . . . , and Fn included in the MRI moving image, the deep learning model learning device may check temporal information of the image frames F1, F2, . . . , and Fn included in the MRI moving image and process frame characteristic learning for the spatial characteristic information on the basis of the checked temporal information. The spatial characteristic information may be sequentially input to the frame characteristic learning model, and the frame characteristic learning model may sequentially output the frame characteristics.

Figure 9:
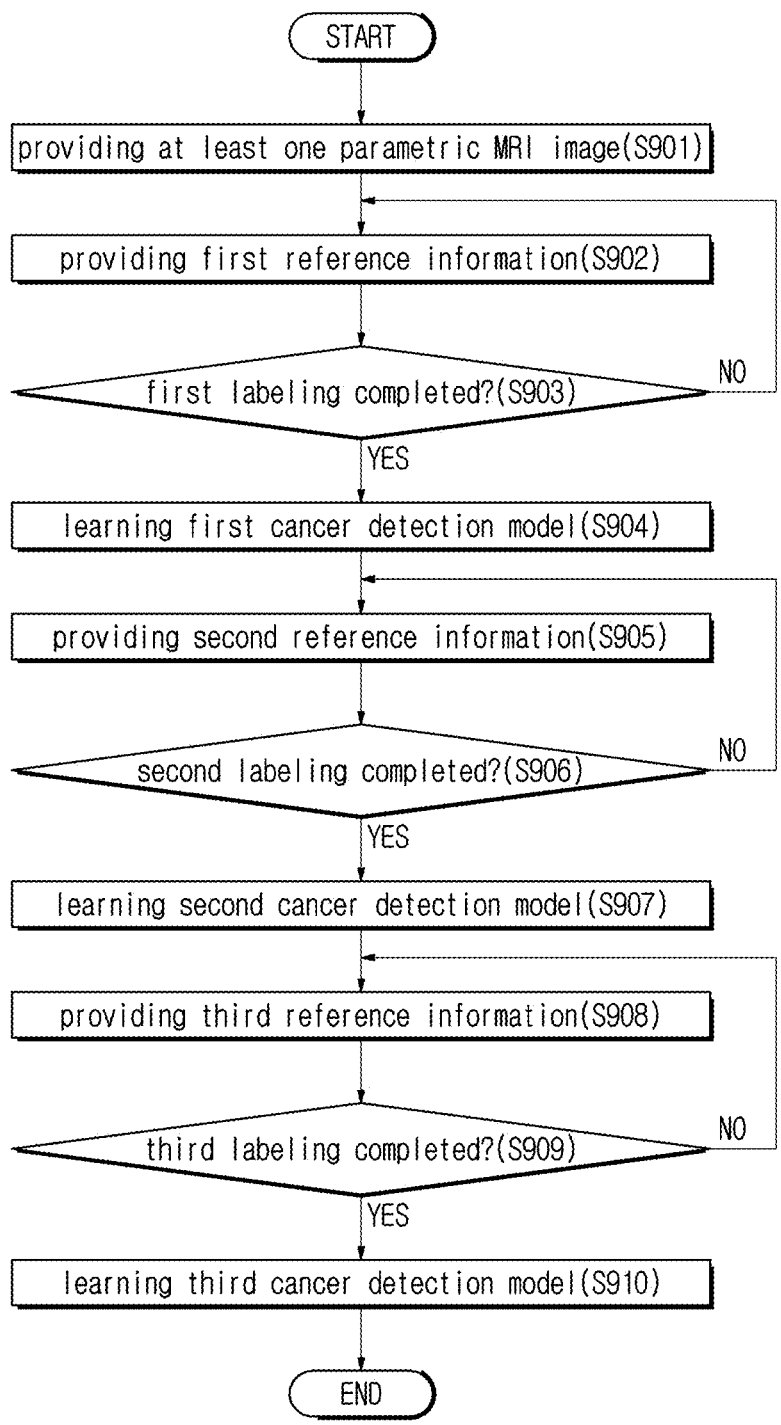
FIG. 9 is a flowchart showing a procedure of the deep learning model learning method according to another exemplary embodiment of the present disclosure.
Figure 10:
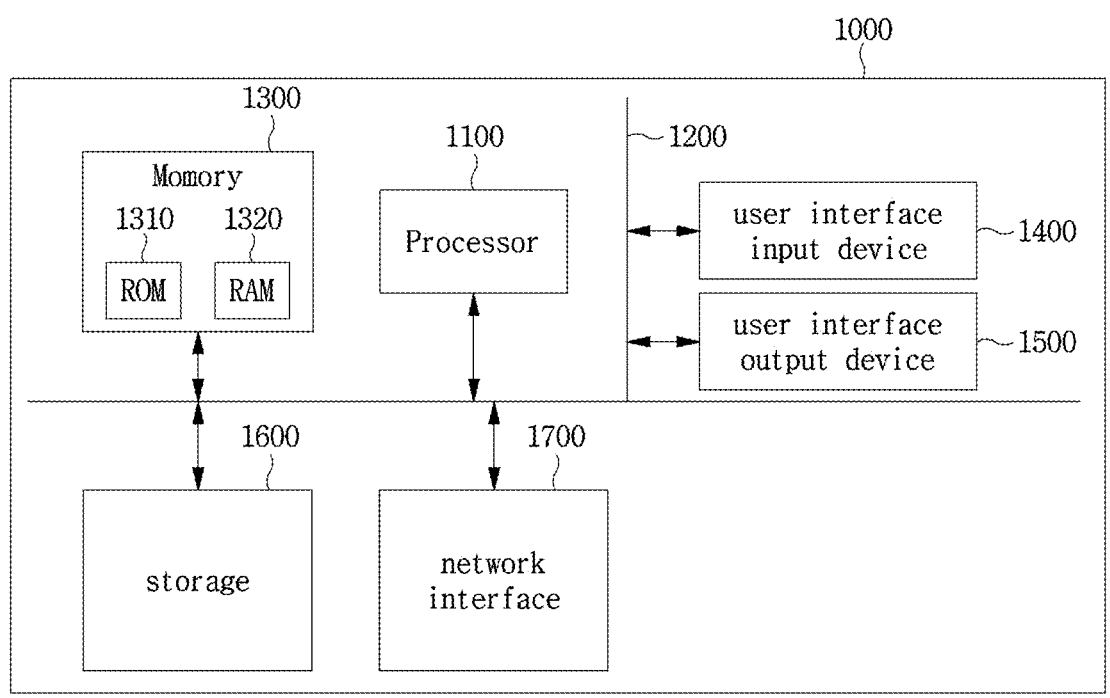
FIG. 10 is a block diagram showing a computing system executing the deep learning model learning method and device thereof according to the exemplary embodiment of the present disclosure.

FIG. 9 is a flowchart showing a procedure of the deep learning model learning method according to another exemplary embodiment of the present disclosure.

The deep learning model learning method according to another exemplary embodiment of the present disclosure is fundamentally similar to the deep learning model learning method according to the exemplary embodiment of the present disclosure. However, in the deep learning model learning method according to another exemplary embodiment of the present disclosure, it is configured such that at least one reference information (i.e., pathology image 205, DWI image 206, DCE signal information 207, etc.) is sequentially provided in conjunction with the labeling operation.

Hereinafter, the deep learning model learning method according to another exemplary embodiment of the present disclosure will be described in detail.

First, step S901 may be performed in the same manner as step S801 described in the deep learning model learning method according to the exemplary embodiment of the present disclosure. That is, the deep learning model learning device may provide at least one parametric MRI image, such as a T1 (T1-weighted) image, a T2 (T2-weighted) image, a T2* (T2 star) image, an ADC (apparent diffusion coefficients) image, a FLAIR (fluid attenuated inversion recovery) image, a STIR (short TI inversion recovery) image, a PWI (perfusion weighted image).

In step S902, the deep learning model learning device may provide information that may be referred to designating a region where cancer is located in the parametric MRI images 203 and 204 of the diagnosis region, that is, one (i.e., first reference information) of reference information (i.e., a pathology image 205, a DWI image 206, DCE signal information 207, and the like).

For example, a diagnosis region of a user (or patient) may be extracted, and a pathology image visualizing a region where cancer tissue is present from the extracted diagnosis region may be constructed, wherein the deep learning model learning device may provide an environment in which such a pathology image may be input. In addition, the deep learning model learning device may display the received pathology image 205 through one region of the screen 220 (refer to FIG. 2c).

In step S903, the deep learning model learning device may provide a user interface 230 capable of performing labeling while displaying the first reference information (i.e., pathology image 205).

The user interface 230 may include at least one parametric MRI image 231 (e.g., T2 image). In addition, the user interface 230 may be connected to an external input device such as a mouse device, a digitizer device, a touch screen device, etc., and may include a predetermined indicator 232 output to a region designated by the external input device. In addition, the deep learning model learning device may set a predetermined region selected through the indicator 232 as a cancer region, and the user interface 230 may include a labeling indicator 233 displaying the corresponding region set as the cancer region.

The deep learning model learning device may perform a labeling operation by setting the predetermined region as the cancer region in the at least one parametric MRI image (e.g., T2 image) through the user interface 230.

In this way, in step S904, when the cancer region is set through the user interface 230, the deep learning model learning device may learn the cancer detection model by inputting the parametric MRI images 203 and 204 of the diagnosis region and outputting the labeled region.

In step S905, the deep learning model learning device checks the second reference information (e.g., DWI (diffusion-weighted imaging) image), and may display the DWI image 206 through one region of the screen 240 (refer to FIG. 2d).

In step S906, the deep learning model learning device may provide a user interface 250 capable of performing labeling while displaying the second reference information (i.e., DWI image 206).

The second user interface 250 may include at least one parametric MRI image 251 (e.g., T2 image). In addition, the second user interface 250 may be connected to an external input device such as a mouse device, a digitizer device, a touch screen device, etc., and may include a predetermined indicator 242 output to a region designated by the external input device. In addition, the deep learning model learning device may set a predetermined region selected through the indicator 252 as a cancer region, and the second user interface 250 may include a labeling indicator 253 displaying the corresponding region set as the cancer region.

In such an environment, the deep learning model learning device may perform a labeling process based on the DWI image 206 by setting the region selected through the second user interface 250 as the cancer region.

In this way, in step S907, when the cancer region is set through the second user interface 250, the deep learning model learning device may learn the cancer detection model by inputting the parametric MRI images 203 and 204 of the diagnosis region and outputting the labeled region.

Additionally, the deep learning model learning device may process the cancer region labeled on the basis of the pathology image 205 as an input.

In step S908, the deep learning model learning device may display the parametric MRI images 203 and 204 and the DCE signal information 207 of the diagnosis region through a third screen 260 (refer to FIG. 2e). In addition, the deep learning model learning device may provide a third user interface 270 capable of performing labeling on a region of the third screen 260 displaying the parametric MRI images 203 and 204 of the diagnosis region and the third reference information (e.g., DCE signal information 207). Here, similar to the first user interface 230 described above, the third user interface 270 may include at least one parametric MRI image 271 (e.g., T2 image), an indicator 272, and a labeling indicator 273.

In the exemplary embodiment of the present disclosure, as the deep learning model learning device is exemplified to provide at least one reference information sequentially, at least one reference information is exemplified as the pathology image, DWI image, DCE signal information, etc., but the present disclosure is not limited thereto, and various changes may be made thereto by those skilled in the art of the present disclosure. In addition, it is apparent that the order of the at least one reference information provided by the deep learning model learning device may also be variously changed.

Furthermore, according to the characteristics of each body organ or each diagnosis region, or a cancer region present in the body organ or diagnosis region, information that may be used as reference information for labeling may be variously changed. Accordingly, the deep learning model learning device may selectively provide the reference information that contributes to the labeling processing of the cancer region on the basis of the characteristics of each body organ or each diagnosis region, or the cancer region present in the body organ or diagnosis region.

For example, in the case where a body organ or a diagnosis region is a prostate region, the deep learning model learning device may provide information, as the first to third reference information, selected from among a T1 contrast image, a T2 contrast image, a PET (positron emission tomography) image, a SPECT (single photon emission computed tomography) image, a DSA (digital subtraction angiography) image, pathology images, DWI image, and DCE signal information.

As another example, in the case where a body organ or a diagnosis region is a liver region, the deep learning model learning device may provide information, as the first to third reference information, selected from the T1 contrast image and the T2 contrast image. As yet another example, in the case where a body organ or a diagnosis region is a brain region, the deep learning model learning device may provide information, as the first to third reference information, selected from FDG-PET image and SPECT image.

In step S909, in such an environment, the deep learning model learning device may perform a labeling process based on the DCE signal information 207 by setting the region selected through the third user interface 270 as the cancer region.

In this way, in step S910, when the cancer region is set through the third user interface 270, the deep learning model learning device may learn the cancer detection model by inputting the parametric Mill images 203 and 204 of the diagnosis region and outputting the labeled region.

Additionally, the deep learning model learning device may process the cancer region, labeled on the basis of the DWI image 206, as an input.

In the exemplary embodiment of the present disclosure, it is exemplified that the deep learning model learning device provides the reference information in the order of the pathology image 205, the DWI image 206, and the DCE signal information 207, but the present disclosure is not limited thereto. The order in which the deep learning model learning device provides the reference information may be variously changed.

In addition, in the exemplary embodiment of the present disclosure, the reference information provided by the deep learning model learning device is exemplified, but the present disclosure is not limited thereto, and the reference information provided by the deep learning model learning device may be variously changed by those skilled in the art of the present disclosure.

In addition, in the exemplary embodiment of the present disclosure, it is exemplified that the deep learning model learning device learns the deep learning model by using the at least one parametric MRI image as a basic input. It is apparent that the exemplary embodiment of present disclosure is not limited thereto, and may be variously changed. For example, the deep learning model learning device may use at least one of the DWI image and DCE signal information, as the input.

In other words, when learning the deep learning model in step S907, the deep learning model learning device may use the DWI image as an input together with at least one parametric MRI image. Likewise, when learning the deep learning model in step S910, the deep learning model learning device may use the DCE signal information as the input together with at least one parametric MRI image.

Additionally, when learning the deep learning model in step S904, the deep learning model learning device may use the pathology information as an input together with at least one parametric MRI image.

First, the device for detecting a prostate cancer region according to an exemplary embodiment of the present disclosure may generate and provide the reference information including the prostate cancer region by using a prostate region detection model and a prostate cancer region detection model. The prostate region detection model and the prostate cancer region detection model according to the exemplary embodiment of the present disclosure may be constructed by the prostate cancer region learning device according to the exemplary embodiment of the present disclosure.

Hereinafter, the device for learning the prostate cancer region and an operation of constructing the prostate region detection model and prostate cancer region detection model by using the same device will be described in detail with reference to FIGS. 11 to 14.

Figure 11:
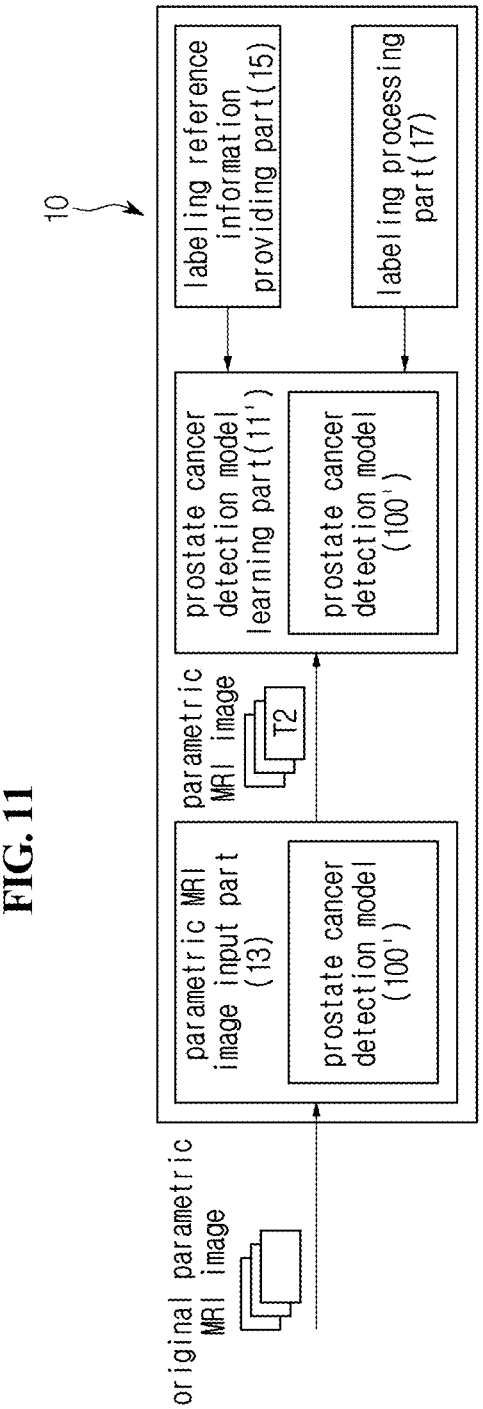
FIG. 11 is a block diagram showing a configuration of a device for learning a prostate cancer detection model according to an exemplary embodiment of the present disclosure.

FIG. 11 is a block diagram showing a configuration of the device for learning the prostate cancer detection model according to the exemplary embodiment of the present disclosure.

Referring to FIG. 11, the device for learning the prostate cancer detection model 1110 may include: a prostate cancer detection model learning part 1111, a parametric MRI image input part 1113, a labeling reference information providing part 1115, and a labeling processing part 1117.

First, the prostate cancer detection model learning part 1111 may learn the prostate cancer detection model on the basis of the convolutional neural network (CNN) technique or the pooling technique. In particular, the prostate cancer detection model learning part 1111 may receive an analysis target image in order to perform learning on the prostate cancer detection model, and may perform a labeling operation, that is, an operation of receiving a specific object or a specific region included in the analysis target image as a prostate cancer region.

In addition, the prostate cancer detection model learning part 1111 may learn the prostate cancer detection model by extracting features of the analysis target image and generating predetermined context information on the basis of the extracted features. In addition, the prostate cancer detection model learning part 1111 may construct a prostate cancer detection model 100 by repeatedly performing learning on the prostate cancer detection model.

The prostate cancer detection model learning part 1111 may receive an MRI image as the analysis target image, and such an input of the analysis target image may be processed by the parametric MRI image input part 1113. The parametric MRI image input part 1113 may provide an MRI image, that is, an image of a user's body photographed by a magnetic resonance imaging (MRI) device to the prostate cancer detection model learning part 1111.

Furthermore, various images may be reconstructed by applying various parameters to the MRI image. In the exemplary embodiment of the present disclosure, the image reconstructed by applying a predetermined parameter to the MRI image is indicated as a parametric MRI image.

Based on the above description, the parametric MRI image input part 1113 may provide at least one parametric MRI image composed on the basis of different parameters to the prostate cancer detection model learning part 1111. Here, the at least one parametric MRI image may include a T2 (T2-weighted) image, an ADC (apparent diffusion coefficients) image, a DWI (diffusion-weighted imaging), etc.

In addition, the parametric MRI image input part 1113 may display the parametric MRI image, providing an MRI image to the prostate cancer detection model learning part 1111, on a display and the like.

Additionally, the parametric MRI image input part 1113 may receive an input of the parametric MRI image based on the MRI image of the body in which the user's prostate is located (hereinafter, referred to as "original parametric MRI image", and may detect the parametric MRI image extracting the prostate region from the original parametric MRI image (hereinafter, referred to as "parametric MRI image of prostate region"). In addition, the parametric MRI image of the prostate region may be provided to the prostate cancer detection model learning part 1111 or may be displayed on a display and the like.

The operation of the parametric MRI image input part 1113 to extract the parametric MRI image of the prostate region from the original parametric MRI image may be performed on the basis of the convolutional neural network (CNN) technique or the pooling technique. For example, the parametric MRI image input part 1113 may construct a predetermined learning model through learning in which the original parametric MRI image is input and the parametric MRI image of the prostate region is output. In addition, the parametric MRI image input part 1113 may detect and output the parametric MRI image of the prostate region, as the original parametric MRI image is input.

Furthermore, since the diagnosis region such as the prostate region is composed in a three-dimensional shape, detecting the characteristics in which an injury appears in a three-dimensional structure of the diagnosis region may improve the performance of the prostate cancer detection model 1100. In addition, a more accurate diagnosis is possible when changes within the diagnosis region, for example, the diffusion of water in the tissue, the increase in contrast medium, and the like are used as diagnostic indicators. In consideration of the above description, the parametric MRI image input part 1113 may input images of DWI, DCE, and the like in the moving image format, so that the three-dimensional structure of the diagnosis region or the changes in the diagnosis region is to be visualized.

Correspondingly, the prostate cancer detection model learning part 1111 may perform learning of the prostate cancer detection model 1100 by using both the parametric MRI image in the still image format and the parametric MRI image in the moving image format. The operation of the cancer detection model learning part 11 to learn the prostate cancer detection model 1100 will be described in detail through the following diagrams and related descriptions.

Meanwhile, the labeling reference information providing part 1115 may provide information contributing to the labeling process of the prostate cancer region.

The prostate of a user (or patient) may be excised through surgery, and a pathology image visualizing a region where cancer tissue is present may be constructed from the excised prostate. In consideration of the above description, the labeling reference information providing part 1115 may provide an environment in which the pathology image may be received as an input, and may display the received pathology image on a display and the like. For example, the pathology image may include an image composed of a pathology map in the image format, the pathology map mapping a region where cancer of the excised prostate is present.

Furthermore, since the T2 image or the ADC image is composed of a two-dimensional image, it may be difficult to check cancer tissue present in a region not displayed on the image itself. In consideration of the above description, the labeling reference information providing part 1115 checks DWI (diffusion-weighted imaging) image indicating information in which water molecules contained in the tissue are diffused in a specific direction, and may display the DWI image on a display and the like. Here, the DWI image may be provided from an MRI device, or may be obtained by processing the MRI image provided from the MRI device.

Likewise, since the T2 image or the ADC image is composed of a two-dimensional image, it may be difficult to check the cancer tissue present in a region not displayed on the image itself or check the characteristics of tissues. In consideration of the above description, the labeling reference information providing part 1115 may check DCE (dynamic contrast enhanced) signal information and establish an environment capable of providing the checked DCE signal information. For example, the labeling processing part 1117 may display at least one parametric MRI image (e.g., T2 image) and provide an indicator for displaying a region designated by a user, and the region selected by the user may be set as the prostate cancer region. In consideration of the above description, the labeling reference information providing part 1115 checks the DCE signal information for the region indicated by the indicator generated and displayed by the labeling processing part 1117, and may display the checked DCE signal information on a display and the like.

The labeling reference information providing part 1115 may display at least one of a pathology image, a DWI image, and DCE signal information on a display and the like.

As another example, the labeling reference information providing part 1115 may sequentially select and display the pathology image, DWI image, and DCE signal information. In particular, the labeling reference information providing part 1115 may sequentially select and display the pathology image, DWI image, and DCE signal information in conjunction with the labeling processing part 1117. For example, the labeling reference information providing part 1115 may display the pathology image together with the T2 image and the ADC image. In addition, in a state in which the pathology image is displayed, as the information firstly labeled the prostate cancer region is input by the labeling processing part 1117, the labeling reference information providing unit 1115 may display the DWI image together with the T2 image and the ADC image. In addition, in a state in which the DWI image is displayed, as the information secondly labeled the prostate cancer region is input by the labeling processing part 1117, the labeling reference information providing part 1115 checks the region indicated by the indicator, and may check and display the DCE signal information corresponding to the relevant region.

Meanwhile, as described above, while providing at least one parametric MRI image (e.g., T2 image), the labeling processing part 1117 may provide an environment in which the labeling, that is, an operation of designating an output value for learning the prostate cancer detection model by the prostate cancer detection model learning part 1111 may be performed.

Specifically, the labeling processing part 1117 outputs at least one parametric MRI image (e.g., T2 image) to a display, and may provide an interface capable of receiving a prostate cancer region, that is, a region where prostate cancer is present in the at least one parametric MRI image (e.g., T2 image) that is output. For example, the labeling processing part 1117 may be connected to an external input device such as a mouse device, a digitizer device, a touch screen device, and the like, outputs a predetermined indicator to the region designated by the external input device, and sets the region selected through the external input device as the prostate cancer region.

Figure 12:
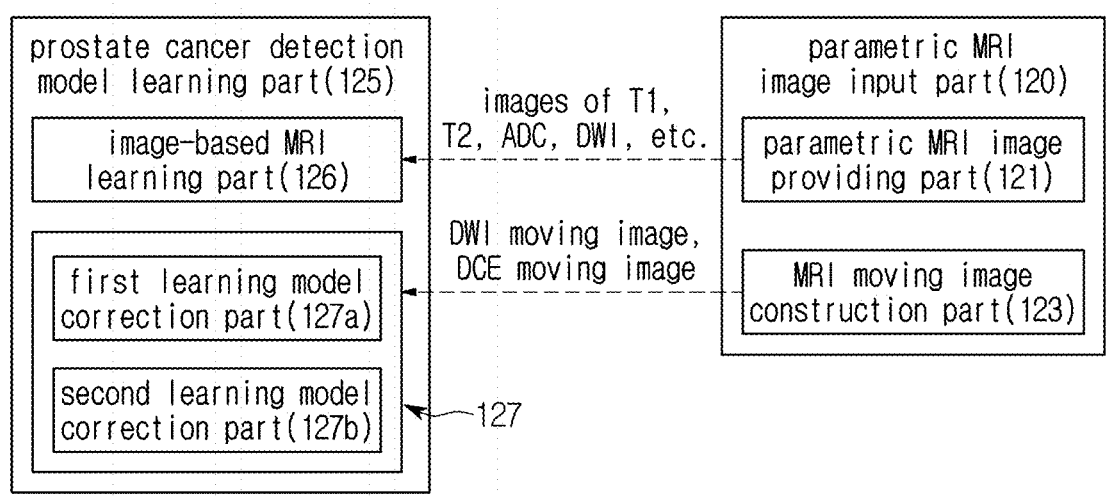
FIG. 12 is a block diagram showing a detailed configuration of a parametric MRI image input part and a prostate cancer detection model learning part provided in the device for learning the prostate cancer detection model according to the exemplary embodiment of the present disclosure.
Figure 13:
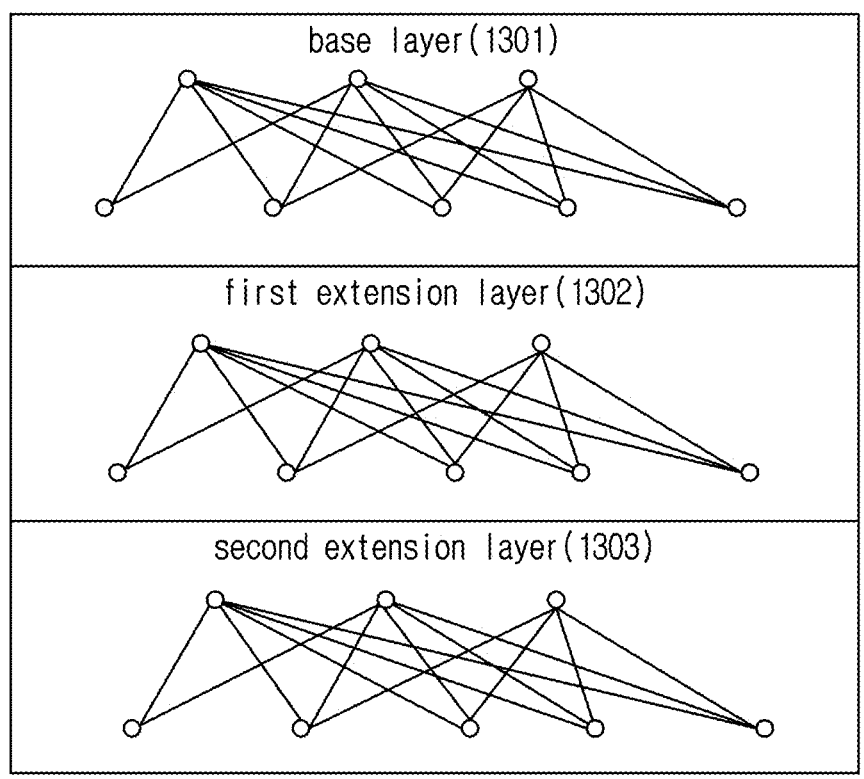
FIG. 13 is a view showing a layer structure of the cancer detection model constructed by the device for learning the prostate cancer detection model according to the exemplary embodiment of the present disclosure.

FIG. 12 is a block diagram showing a detailed configuration of a parametric MRI image input part and a prostate cancer detection model learning part provided in the device for learning the prostate cancer detection model according to the exemplary embodiment of the present disclosure.

Referring to FIG. 12, the parametric MRI image input part 120 may include a parametric MRI providing part 121 and an MRI moving image construction part 123. The parametric MRI providing part 121 may check and provide the parametric MRI image in the still image format, for example, images of T1, T2, ADC, DWI, etc., to the prostate cancer detection model learning part 125. In addition, the MRI moving image construction part 123 may construct and provide a parametric MRI image in the moving image format (e.g., images of DWI, DCE, etc.), in which a temporal change occurs. Specifically, at each predetermined time unit, the MRI moving image construction part 123 continuously photographs DWI images indicating the arranged state of cells by using the fine motility of water molecules in the tissue, and may construct the DWI moving image by combining the continuously photographed DWI images. As another example, at each predetermined time unit, the MRI moving image construction part 123 continuously photographs DCE images evaluating a blood flow state of the tissue by measuring a change in the contrast enhancement intensity after injection of a contrast agent, and may construct the DCE moving image by combining the continuously photographed DCE images.

The cancer detection model learning part 125 may include an image-based MRI learning part 126 and a learning model correction part 127. First, the image-based MRI learning part 126 may perform learning on the cancer detection model by performing learning on the parametric MRI in the image format. In this case, the image-based MRI learning part 126 may construct a base layer of the cancer detection model by applying the convolutional neural network (CNN) technique or the pooling technique to at least one parametric MRI image provided by the parametric MRI providing part 121. In this case, the parametric MRI image in use may be variously changed. After the base layer of the cancer detection model is constructed through the image-based MRI learning part 126, the learning model correction part 127 may perform correction for the cancer detection model by using the MRI moving image provided by the MRI moving image construction part 123 so as to construct an extension layer of the cancer detection model. For example, the learning model correction part 127 may construct the extension layer so as to detect characteristics according to the temporal arrangement of each frame, after detecting spatial characteristics of each frame included in the MRI moving image. In this case, the spatial characteristics of each frame may be constructed on the basis of the convolutional neural network (CNN) technique or the pooling technique, and the characteristics according to the temporal arrangement of each frame may be constructed on the basis of the learning method of the recurrent neural network (RNN).

Furthermore, the learning model correction part 127 may be configured to construct a plurality of extension layers step by step. For example, the learning model correction part 127 may include a first correction part 127a and a second correction part 127b. The first correction part 127a is configured to construct a first extension layer of the cancer detection model by using a first MRI moving image, and the second correction unit 127b is configured to construct a second extension layer of the cancer detection model by using a second MRI moving image. Accordingly, the cancer detection model may be configured such that a base layer 1301, a first extension layer 1302, and a second extension layer 1303 are connected one after another in series. Furthermore, the first MRI moving image and the second MRI moving image may be different types of MRI moving images, respectively. For example, the first MRI moving image may be the DWI moving image constructed by combining successively photographed DWI images, and the second MRI moving image may be the DCE moving image constructed by combining successively photographed DCE images.

Figure 14:
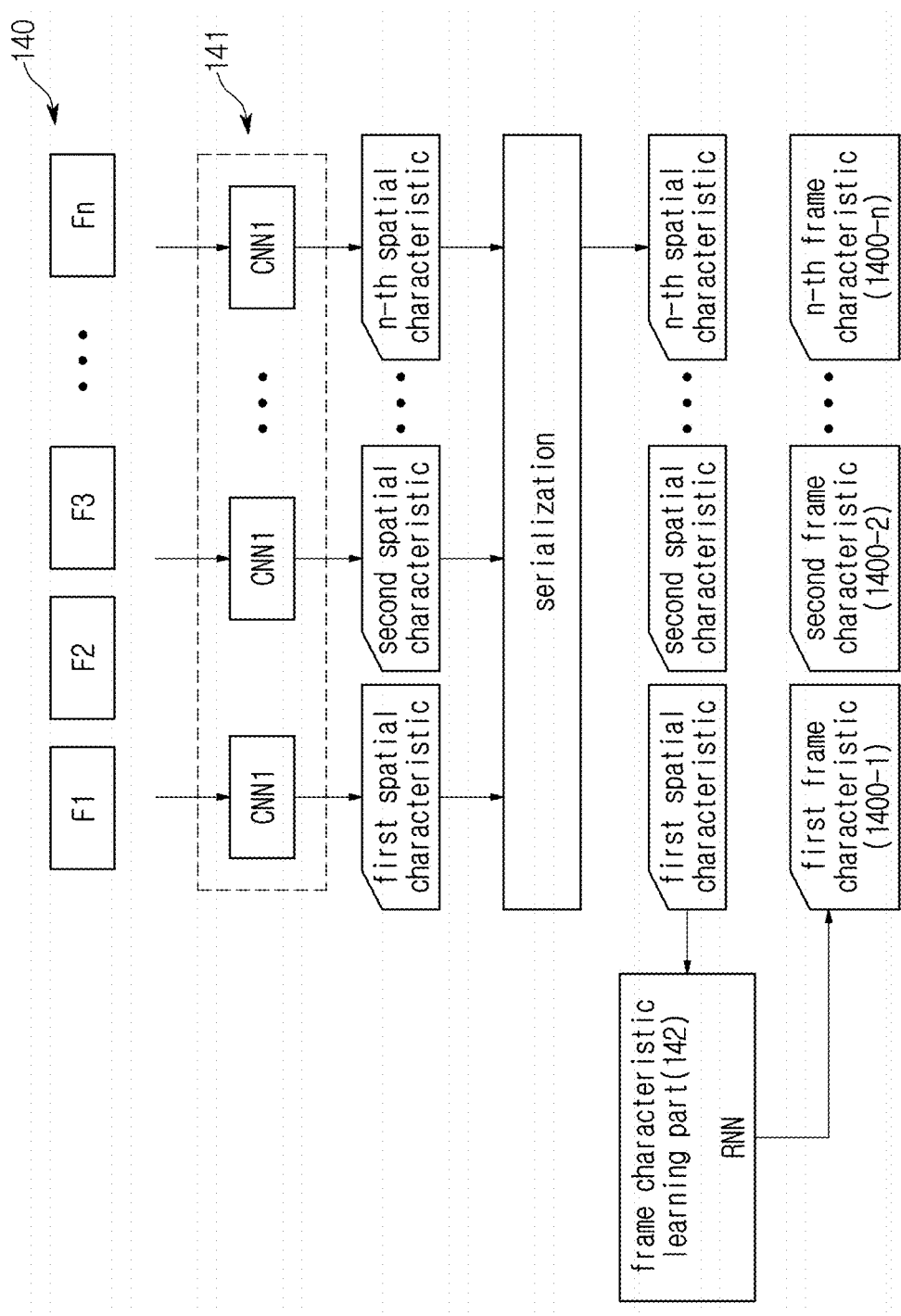
FIG. 14 is a view showing a detailed configuration of the learning model correction part of FIG. 12.

FIG. 14 is a view showing a detailed configuration of the learning model correction part of FIG. 12.

The learning model correction part 140 may include a spatial characteristic learning part 141 and a frame characteristic learning part 142.

The spatial characteristic learning part 141 may construct a spatial characteristic learning model by performing learning on each of the image frames F1, F2, . . . , and Fn included in the MRI moving image, and preferably, may construct the spatial characteristic learning model on the basis of the learning method of the convolutional neural networks (CNN).

When constructing the spatial characteristic learning model of the spatial characteristic learning part 141, the information on the time or arrangement order corresponding to the image frames F1, F2, . . . , and Fn may be considered. For example, the spatial characteristic learning model may be provided with the CNN corresponding to the number of image frames F1, F2, . . . , and Fn included in the MRI moving image, and the spatial characteristic learning part 141 may be configured such that the first image frame F1 is transmitted as an input of a first CNN, the second image frame F2 is transmitted as an input of a second CNN, and the n-th image frame Fn is transmitted as an input of an n-th CNN.

Corresponding to the above description, the plurality of CNNs provided in the spatial characteristic learning model 141 may output a plurality of spatial characteristics corresponding to each of the plurality of image frames F1, F2, . . . , and Fn, and the spatial characteristic learning part 141 may sequentially arrange the plurality of spatial characteristics described above to construct sequential data. In this case, the spatial characteristic learning part 141 may construct the sequential data in consideration of information on the time or arrangement order corresponding to the image frames F1, F2, . . . , and Fn.

Meanwhile, the frame characteristic learning part 142 receives an input of the plurality of spatial characteristics composed of the sequential data, and may perform learning to detect characteristics (i.e., frame characteristics) regarding the relationship between image frames. Preferably, the frame characteristic learning part 142 may construct a frame characteristic learning model on the basis of the learning method of the recurrent neural network (RNN).

The recurrent neural network (RNN) serves as a deep learning technique that considers both current and past data at the same time, and in the recurrent neural network (RNN), the connection between units constituting the artificial neural network represents the neural network that constitutes the directed cycle. Furthermore, various methods may be used for the structure capable of constituting the recurrent neural network (RNN). For example, representative examples include: a fully recurrent network, a Hopfield network, an Elman Network, and an echo state network (ESN), a long short term memory network (LSTM), a bi-directional RNN, a continuous-time RNN (CTRNN), a hierarchical RNN, a secondary RNN, etc. In addition, as a method for training the recurrent neural network (RNN), a gradient descent method, a Hessian free optimization, a global optimization method, and the like may be used.

Meanwhile, since the spatial characteristic information is the information extracted from the image frames F1, F2, . . . , and Fn included in the MRI moving image, the frame characteristic learning part 142 may check temporal information of the image frame F1, F2, . . . , and Fn included in the MRI moving image and process the frame characteristic learning for the spatial characteristic information on the basis of the checked temporal information. The spatial characteristic information may be sequentially input to the frame characteristic learning model 142, and the frame characteristic learning model may sequentially output the frame characteristics 1400-1, 1400-2, . . . , and 1400-n.

The exemplary methods described herein were expressed by a series of operations for clear description, but it does not limit the order of performing the steps, and if necessary, the steps may be performed simultaneously or in different orders. In order to achieve the method of the present disclosure, other steps may be added to the exemplary steps, or the other steps except for some steps may be included, or additional other steps except for some steps may be included.

Various embodiments described herein are provided to not arrange all available combinations, but explain a representative aspect of the present disclosure and the configurations about the embodiments may be applied individually or in combinations of at least two of them.

Further, various embodiments of the present disclosure may be implemented by hardware, firmware, software, or combinations thereof. When hardware is used, the hardware may be implemented by at least one of ASICs (Application Specific Integrated Circuits), DSPs (Digital Signal Processors), DSPDs (Digital Signal Processing Devices), PLDs (Programmable Logic Devices), FPGAs (Field Programmable Gate Arrays), a general processor, a controller, a micro controller, and a micro-processor. The scope of the present disclosure includes software and device-executable commands (for example, an operating system, applications, firmware, programs) that make the method of the various embodiments of the present disclosure executable on a machine or a computer, and non-transitory computer-readable media that keeps the software or commands and can be executed on a device or a computer.

INDUSTRIAL APPLICABILITY

The present invention may be applied to a medical field based on deep learning.

The invention claimed is:

1. A deep learning model learning device for a cancer region, the deep learning model learning device comprising:
a parametric MRI image input part for inputting an image corresponding to a diagnosis region, inputting at least one parametric MRI (Magnetic Resonance Imaging) image constructed on the basis of parameters different from each other, and constructing and providing an MRI moving image by using the at least one parametric MRI image;
a cancer detection model learning part for receiving an input of the at least one parametric MRI image and the MRI moving image corresponding to the diagnosis region, and learning a deep learning model on the basis of information labeling the cancer region;
a labeling reference information providing part for providing at least one reference information contributing to the labeling of the cancer region; and
a labeling processing part for checking the cancer region input on the basis of the at least one reference information and processing the labeling of the checked cancer region,
wherein the cancer detection model learning part comprises an image-based MRI learning part that constructs a base layer of the deep learning model through learning on the at least one parametric MRI image,
the cancer detection model learning part comprises a learning model correction part that constructs an extension layer of the deep learning model through learning on the MRI moving image, and
the learning model correction part comprises:
a first learning model correction part for constructing a first extension layer of the deep learning model through learning on a first MRI moving image; and
a second learning model correction part for constructing a second extension layer of the deep learning model through learning on a second MRI moving image.

2. The deep learning model learning device of claim 1, wherein the at least one parametric MRI image comprises at least one of a T1 (T1-weighted) image, a T2 (T2-weighted) image, a T2* (T2 star) image, an ADC (apparent diffusion coefficients) image, a FLAIR (fluid attenuated inversion recovery) image, a STIR (short T1 inversion recovery) image, a PWI (perfusion weighted image), and a DCE (dynamic contrast enhanced) image.

3. The deep learning model learning device of claim 1, wherein the at least one reference information comprises at least one of a pathology image displayed by imaging a region where cancer is present in an excised diagnosis region, a DWI (diffusion-weighted imaging) image, and DCE (dynamic contrast enhanced) signal information.

4. The deep learning model learning device of claim 3, wherein the parametric MRI image input part constructs a DWI moving image by sequentially arranging the DWI images in time.

5. The deep learning model learning device of claim 3, wherein the parametric MRI image input part constructs a DCE moving image by sequentially arranging DCE images in time.

6. The deep learning model learning device of claim 1, wherein the first MRI moving image is a DWI moving image constructed by sequentially arranging DWI images in time, and the second MRI moving image is a DCE moving image construct by sequentially arranging DCE images in time.

* * * * *